(12) United States Patent
Laufer et al.

(10) Patent No.: US 10,167,289 B2
(45) Date of Patent: Jan. 1, 2019

(54) PYRAZOLOPYRIMIDINE COMPOUNDS

(71) Applicant: University Health Network, Toronto (CA)

(72) Inventors: Radoslaw Laufer, Oakville (CA); Grace Ng, Markham (CA); Sze-Wan Li, Toronto (CA); Heinz W. Pauls, Oakville (CA); Yong Liu, Oakville (CA); Narendra Kumar B. Patel, Brampton (CA)

(73) Assignee: University Health Network, Toronto (CA)

( * ) Notice: Subject to any disclaimer, the term of this patent is extended or adjusted under 35 U.S.C. 154(b) by 0 days.

(21) Appl. No.: 15/598,402

(22) Filed: May 18, 2017

(65) Prior Publication Data

US 2017/0320881 A1    Nov. 9, 2017

Related U.S. Application Data

(60) Division of application No. 14/926,977, filed on Oct. 29, 2015, now Pat. No. 9,657,025, which is a continuation of application No. PCT/CA2014/051091, filed on Nov. 14, 2014.

(30) Foreign Application Priority Data

Nov. 15, 2013    (WO) ................ PCT/CA2013/000957

(51) Int. Cl.
  *C07D 487/04*    (2006.01)
  *C07D 519/00*    (2006.01)

(52) U.S. Cl.
  CPC ......... *C07D 487/04* (2013.01); *C07D 519/00* (2013.01)

(58) Field of Classification Search
  CPC .................................................. C07D 487/04
  See application file for complete search history.

(56) References Cited

U.S. PATENT DOCUMENTS

| | | | |
|---|---|---|---|
| 4,021,556 A | 5/1977 | Springer et al. |
| 6,060,478 A | 5/2000 | Gilligan et al. |
| 6,124,289 A | 9/2000 | He et al. |
| 6,191,131 B1 | 2/2001 | He et al. |
| 6,313,124 B1 | 11/2001 | He et al. |
| 6,372,743 B1 | 4/2002 | Darrow et al. |
| 6,476,038 B1 | 11/2002 | Darrow et al. |
| 7,723,336 B2 | 5/2010 | Vaccaro et al. |
| 9,573,954 B2 | 2/2017 | Liu et al. |
| 9,657,025 B2 | 5/2017 | Laufer et al. |
| 2002/0147338 A1 | 10/2002 | Gilligan et al. |
| 2004/0043998 A1 | 3/2004 | Kato et al. |
| 2004/0254220 A1 | 12/2004 | Bressi et al. |
| 2005/0187219 A1 | 8/2005 | Guzi et al. |
| 2005/0229333 A1 | 10/2005 | Glenn et al. |
| 2006/0025426 A1 | 2/2006 | Fraley |
| 2006/0079536 A1 | 4/2006 | Yasuma et al. |
| 2006/0089362 A1 | 4/2006 | Seno et al. |
| 2006/0106019 A1 | 5/2006 | Bernard |
| 2006/0276475 A1 | 12/2006 | Vu et al. |
| 2007/0078136 A1 | 4/2007 | Vaccaro et al. |
| 2007/0082900 A1 | 4/2007 | Guzi et al. |
| 2007/0173505 A1 | 7/2007 | Peng et al. |
| 2007/0232623 A1 | 10/2007 | Gudmundsson et al. |
| 2010/0029657 A1 | 2/2010 | Levin et al. |
| 2010/0216798 A1 | 8/2010 | Nakai et al. |
| 2011/0190319 A1 | 8/2011 | Combs et al. |
| 2011/0281866 A1 | 11/2011 | Ren et al. |
| 2012/0003215 A1 | 1/2012 | Babaoglu et al. |
| 2012/0059162 A1 | 3/2012 | Kusakabe et al. |
| 2012/0077814 A1 | 3/2012 | Wang et al. |
| 2012/0083498 A1 | 4/2012 | Kashanchi |
| 2012/0095005 A1 | 4/2012 | Allen et al. |
| 2012/0149708 A1 | 6/2012 | Kashanchi |

(Continued)

FOREIGN PATENT DOCUMENTS

| | | |
|---|---|---|
| CA | 2656419 A1 | 12/2007 |
| CA | 2693915 A1 | 1/2009 |

(Continued)

OTHER PUBLICATIONS

International Search Report dated Jan. 22, 2015 for PCT Application No. PCT/CA2014/051091.

(Continued)

*Primary Examiner* — Brian E McDowell

(74) *Attorney, Agent, or Firm* — McCarter & English, LLP; Steven G. Davis; Wei Song

(57) ABSTRACT

The present teachings provide a compound represented by the following structural formula: (Formula (I)); or a pharmaceutically acceptable salt thereof. Also described are pharmaceutical compositions and methods of use thereof.

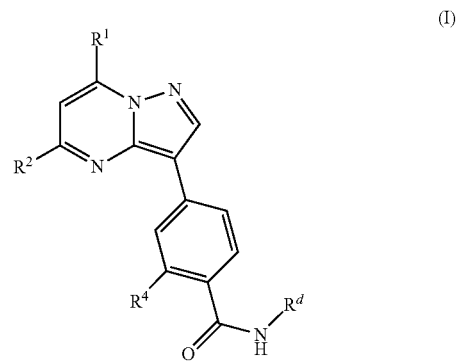

16 Claims, No Drawings

(56) References Cited

U.S. PATENT DOCUMENTS

| | | |
|---|---|---|
| 2012/0322791 A1 | 12/2012 | Siddigui et al. |
| 2014/0038953 A1 | 2/2014 | Yu et al. |
| 2014/0249147 A1 | 9/2014 | Blum et al. |
| 2014/0329807 A1 | 11/2014 | Xu et al. |
| 2015/0299203 A1 | 10/2015 | Liu et al. |
| 2016/0137651 A1 | 5/2016 | Laufer et al. |
| 2017/0217966 A1 | 8/2017 | Liu et al. |

FOREIGN PATENT DOCUMENTS

| | | |
|---|---|---|
| EP | 2402337 A1 | 1/2012 |
| EP | 2460805 A1 | 6/2012 |
| JP | H04156452 A | 5/1992 |
| JP | H04156453 A | 5/1992 |
| WO | 200123387 A2 | 4/2001 |
| WO | 2004022559 A1 | 3/2004 |
| WO | 2004052315 A2 | 6/2004 |
| WO | 2004087707 A1 | 10/2004 |
| WO | 2005063766 A2 | 7/2005 |
| WO | 2007044441 A2 | 4/2007 |
| WO | 2007147647 A1 | 12/2007 |
| WO | 2008025822 A1 | 3/2008 |
| WO | 2008045267 A2 | 4/2008 |
| WO | 2008056176 A1 | 5/2008 |
| WO | 2009014620 A1 | 1/2009 |
| WO | 2010086040 A1 | 8/2010 |
| WO | 2011013729 A1 | 2/2011 |
| WO | 2011090935 A1 | 7/2011 |
| WO | 2011151259 A1 | 12/2011 |
| WO | 2012032031 A1 | 3/2012 |
| WO | 2012/080230 A1 | 6/2012 |
| WO | 2012080229 A1 | 6/2012 |
| WO | 2012080236 A1 | 6/2012 |
| WO | 2012100229 A2 | 7/2012 |
| WO | 2012136531 A1 | 10/2012 |
| WO | 2014075168 A1 | 5/2014 |
| WO | 2015070349 A1 | 5/2015 |

OTHER PUBLICATIONS

International Search Report dated Feb. 28, 2014 for PCT Application No. PCT/CA2013/000957.

Nie Z. et al., "Structure-based design, synthesis, and study of pyrazolo[1,5-a][1,3,5]triazine derivatives as potent inhibitors of protein kinase CK2," Bioorganic and Medicinal Chemistry Letters, vol. 17, pp. 4191-4195, 2007.

Liu, et al., U.S. Appl. No. 15/434,275, filed Feb. 16, 2017.

PYRAZOLOPYRIMIDINE COMPOUNDS

RELATED APPLICATIONS

This application is a divisional application of U.S. application Ser. No. 14/926,977, filed on Oct. 29, 2015 and now U.S. Pat. No. 9,657,025, which, in turn, is a continuation of International Application No. PCT/CA2014/051091, filed Nov. 14, 2014, which claims benefit of International Application No. PCT/CA2013/000957, filed on Nov. 15, 2013. The entire contents of each of the aforementioned applications are incorporated herein by reference.

BACKGROUND OF THE INVENTION

Protein kinases have been the subject of extensive study in the search for new therapeutic agents in various diseases, for example, cancer. Protein kinases are known to mediate intracellular signal transduction by effecting a phosphoryl transfer from a nucleoside triphosphate to a protein acceptor that is involved in a signaling pathway. There are a number of kinases and pathways through which extracellular and other stimuli cause a variety of cellular responses to occur inside the cell.

Human TTK protein kinase (TTK), also known as tyrosine threonine kinase, dual specificity protein kinase TTK, Monopolar Spindle 1 (Mps1) and Phosphotyrosine-Picked Threonine Kinase (PYT), is a conserved multispecific kinase that is capable of phosphorylating serine, threonine and tyrosine residues when expressed in E. coli (Mills et al., J. Biol. Chem. 22(5): 16000-16006 (1992)). TTK mRNA is not expressed in the majority of physiologically normal tissues in human (Id). TTK mRNA is expressed in some rapidly proliferating tissues, such as testis and thymus, as well as in some tumors (for example, TTK mRNA was not expressed in renal cell carcinoma, was expressed in 50% of breast cancer samples, was expressed in testicular tumors and ovarian cancer samples) (Id). TTK is expressed in some cancer cell lines and tumors relative to normal counterparts (Id.; see also WO 02/068444 A1).

Therefore, agents which inhibit a protein kinase, in particular TTK, have the potential to treat cancer. There is a need for additional agents which can act as protein kinase inhibitors, in particular TTK inhibitors.

In addition, cancer recurrence, drug resistance or metastasis is one of the major challenges in cancer therapies. Cancer patients who responded favorably to the initial anti-cancer therapy often develop drug resistance and secondary tumors that lead to the relapse of the disease. Recent research evidences suggest that the capability of a tumor to grow and propagate is dependent on a small subset of cells within the tumor. These cells are termed tumor-initiating cells (TICs) or cancer stem cells. It is thought that the TICs are responsible for drug resistance, cancer relapse and metastasis. Compounds that can inhibit the growth and survival of these tumor-initiating cells can be used to treat cancer, metastasis or prevent recurrence of cancer. Therefore, a need exists for new compounds that can inhibit the growth and survival of tumor-imitating cells.

SUMMARY OF THE INVENTION

Applicants have now discovered that certain pyrazolopyrimidine compounds are potent kinase inhibitors, such as TTK protein kinase (see Example B). Applicants have also discovered that these compounds have potent anticancer activity against breast cancer, colon cancer, and ovarian cancer cells in cell culture study (see Examples C-D). Based on these discoveries, pyrazolopyrimidine compounds, pharmaceutical compositions thereof, and methods of treating cancer with the pyrazolopyrimidine compounds are disclosed herein.

The present teachings are directed, at least in part, to a compound represented by the following structural formula:

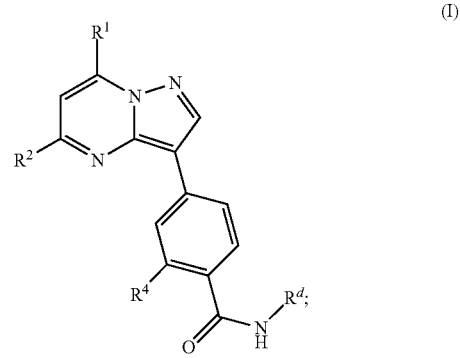

or a pharmaceutically acceptable salt thereof, wherein:
$R^1$ is —NH—$CH_2$-Cy,
Cy is $C_3$-$C_4$ cycloalkyl optionally substituted with one or two groups selected from alkyl and hydroxyl;
$R^2$ is —O-pyridinyl; —NH—($C_2$-$C_6$)hydroxyalkyl optionally substituted with cyclopropyl or isopropyl; or —NH—($C_3$-$C_6$)cycloalkyl optionally substituted with hydroxyl or ($C_1$-$C_2$)hydroxylalkyl;
$R^4$ is selected from hydrogen, halogen, and ($C_1$-$C_3$)alkyl; and
$R^d$ is cyclopropyl. Preferably, $R^4$ is chlorine or methyl.

In one embodiment, the present teachings include a pharmaceutical composition comprising a pharmaceutically acceptable carrier or diluent and a compound represented by structural formula (I) described above or a pharmaceutically acceptable salt thereof.

In another embodiment, the present teachings provide a method of treating a subject having cancer comprising administering to the subject an effective amount of a compound of structural formula (I) or a pharmaceutically acceptable salt thereof.

Another embodiment of the present teachings provides a method of inhibiting TTK activity in a subject in need of inhibition of TTK activity, comprising administering to the subject an effective amount of a compound represented by Structural Formula (I) or a pharmaceutically acceptable salt thereof.

Another embodiment of the present teachings includes the use of a compound represented by Structural Formula (I) or a pharmaceutically acceptable salt thereof in therapy. In some embodiments, the therapy is for treating a subject with cancer. Alternatively, the therapy is for inhibiting TTK activity in a subject in need of inhibition of TTK activity.

Another embodiment of the present teachings includes the use of a compound represented by Structural Formula (I) or a pharmaceutically acceptable salt thereof for the manufacture of a medicament for treating a subject with cancer.

Another embodiment of the present teachings includes the use of a compound represented by Structural Formulas (I) or a pharmaceutically acceptable salt thereof for the manufacture of a medicament for inhibiting TTK activity in a subject in need of inhibition of TTK activity.

DETAILED DESCRIPTION OF THE INVENTION

In one embodiment, the present teachings are directed to a compound represented by Structural Formula (I) or a pharmaceutically acceptable salt thereof. The invention also includes the compounds depicted by structure and/or described by name in the Exemplification, and includes both the neutral forms and as well as pharmaceutically acceptable salts thereof. Treatments with and/or uses of these compounds (including neutral forms and pharmaceutically acceptable salts thereof) as described herein are also included in the invention. Specific examples of compounds of the invention are shown below:

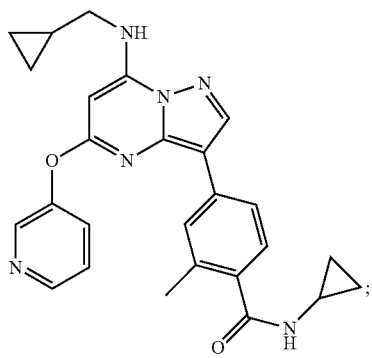 [SMILES: Cc1cc(-c2cnn3c(NCC4CC4)cc(Oc4cccnc4)nc23)ccc1C(=O)NC1CC1]

or a pharmaceutically acceptable salt thereof.

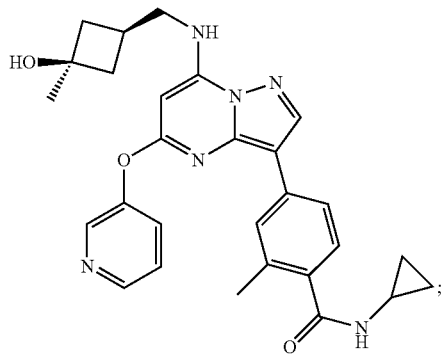 [SMILES: Cc1cc(-c2cnn3c(NC[C@H]4C[C@@](C)(O)C4)cc(Oc4cccnc4)nc23)ccc1C(=O)NC1CC1]

or a pharmaceutically acceptable salt thereof;

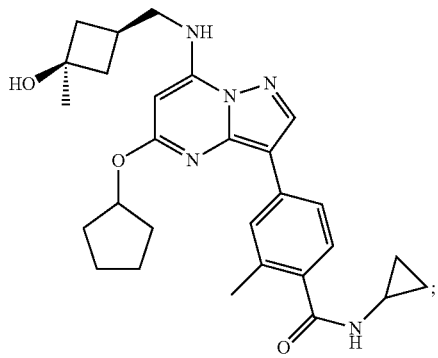 [SMILES: Cc1cc(-c2cnn3c(NC[C@H]4C[C@@](C)(O)C4)cc(OC4CCCC4)nc23)ccc1C(=O)NC1CC1]

or a pharmaceutically acceptable salt thereof; and

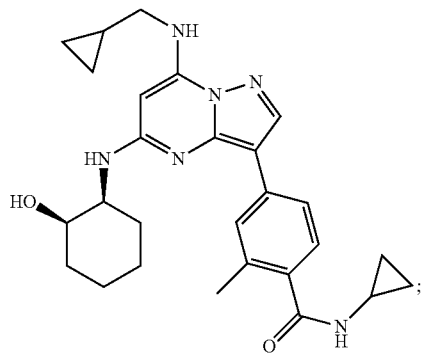 [SMILES: Cc1cc(-c2cnn3c(NCC4CC4)cc(N[C@H]4CCCC[C@H]4O)nc23)ccc1C(=O)NC1CC1]

or a pharmaceutically acceptable salt thereof.

The term "alkyl" used alone or as part of a larger moiety, such as "hydroxyalkyl", and the like, means saturated aliphatic straight-chain or branched monovalent hydrocarbon radical. Unless otherwise specified, an alkyl group typically has 1-6 carbon atoms, i.e., $(C_1-C_6)$alkyl. As used herein, a "$(C_1-C_6)$alkyl" group is means a radical having from 1 to 6 carbon atoms in a linear or branched arrangement.

"Cycloalkyl" means a saturated aliphatic cyclic hydrocarbon radical optionally containing one or more double bonds. It can be monocyclic, bicyclic (e.g., a bridged bicyclic ring), poly cyclic (e.g., tricyclic), or fused. For example, monocyclic $(C_3-C_7)$cycloalkyl means a radical having from 3-7 carbon atoms arranged in a monocyclic ring. A $(C_3-C_7)$ cycloalkyl includes, but is not limited to, cyclopropyl, cyclobutyl, cyclopentyl, cyclohexyl, and cycloheptyl.

Certain of the compounds described herein may exist in various stereoisomeric or tautomeric forms. Stereoisomers are compounds which differ only in their spatial arrangement. When a disclosed compound is named or depicted by structure without indicating stereochemistry, it is understood that the name or structure encompasses all possible stereoisomers, tautomers, geometric isomers or a combination thereof.

When a geometric isomer is depicted by name or structure, it is to be understood that the geometric isomeric purity of the named or depicted geometric isomer is at least 60%, 70%, 80%, 90%, 99% or 99.9% pure by weight. Geometric isomeric purity is determined by dividing the weight of the named or depicted geometric isomer in the mixture by the total weight of all of the geomeric isomers in the mixture.

Racemic mixture means 50% of one enantiomer and 50% of is corresponding enantiomer. The present teachings encompass all enantiomerically-pure, enantiomerically-enriched, diastereomerically pure, diastereomerically enriched, and racemic mixtures, and diastereomeric mixtures of the compounds described herein.

Enantiomeric and diastereomeric mixtures can be resolved into their component enantiomers or stereoisomers by well known methods, such as chiral-phase gas chromatography, chiral-phase high performance liquid chromatography, crystallizing the compound as a chiral salt complex, or crystallizing the compound in a chiral solvent. Enantiomers and diastereomers can also be obtained from diastereomerically- or enantiomerically-pure intermediates, reagents, and catalysts by well known asymmetric synthetic methods.

When a compound is designated by a name or structure that indicates a single enantiomer, unless indicated otherwise, the compound is at least 60%, 70%, 80%, 90%, 99% or 99.9% optically pure (also referred to as "enantiomerically pure"). Optical purity is the weight in the mixture of the named or depicted enantiomer divided by the total weight in the mixture of both enantiomers.

When the stereochemistry of a disclosed compound is named or depicted by structure, and the named or depicted structure encompasses more than one stereoisomer (e.g., as in a diastereomeric pair), it is to be understood that one of the encompassed stereoisomers or any mixture of the encompassed stereoisomers are included. It is to be further understood that the stereoisomeric purity of the named or depicted stereoisomers at least 60%, 70%, 80%, 90%, 99% or 99.9% by weight. The stereoisomeric purity in this case is determined by dividing the total weight in the mixture of the stereoisomers encompassed by the name or structure by the total weight in the mixture of all of the stereoisomers.

Included in the present teachings are pharmaceutically acceptable salts of the compounds disclosed herein. The disclosed compounds have basic amine groups and therefore can form pharmaceutically acceptable salts with pharmaceutically acceptable acid(s). Suitable pharmaceutically acceptable acid addition salts of the compounds described herein include salts of inorganic acids (such as hydrochloric acid, hydrobromic, phosphoric, nitric, and sulfuric acids) and of organic acids (such as, acetic acid, benzenesulfonic, benzoic, methanesulfonic, and p-toluenesulfonic acids). Compounds of the present teachings with acidic groups such as carboxylic acids can form pharmaceutically acceptable salts with pharmaceutically acceptable base(s). Suitable pharmaceutically acceptable basic salts include ammonium salts, alkali metal salts (such as sodium and potassium salts) and alkaline earth metal salts (such as magnesium and calcium salts). Compounds with a quaternary ammonium group also contain a counteranion such as chloride, bromide, iodide, acetate, perchlorate and the like. Other examples of such salts include hydrochlorides, hydrobromides, sulfates, methanesulfonates, nitrates, benzoates and salts with amino acids such as glutamic acid.

Compounds described herein can inhibit various kinases, including the TTK. Thus, generally, compounds described herein are useful in the treatment of diseases or conditions associated with such kinases. In some embodiments, compounds described herein can inhibit TTK.

In one embodiment, the compounds described herein are TTK inhibitors, and are useful for treating diseases, such as cancer, associated with such kinase(s).

Another aspect of the present teachings relates to a method of treating a subject with cancer comprising administering to the subject an effective amount of a compound described herein. In one embodiment, the compounds described herein inhibit the growth of a tumor. For example, the compounds described herein inhibit the growth of a tumor that overexpresses TTK.

Cancers that can be treated (including reduction in the likelihood of recurrence) by the methods of the present teachings include lung cancer, breast cancer, colon cancer, brain cancer, neuroblastoma, prostate cancer, melanoma, glioblastoma multiform, ovarian cancer, lymphoma, leukemia, melanoma, sarcoma, paraneoplasia, osteosarcoma, germinoma, glioma and mesothelioma. In one embodiment, the cancer is selected from leukemia, acute myeloid leukemia, chronic myelogenous leukemia, breast cancer, brain cancer, colon cancer, colorectal cancer, head and neck cancer, hepatocellular carcinoma, lung adenocarcinoma, metastatic melanoma, pancreatic cancer, prostate cancer, ovarian cancer and renal cancer. In one embodiment, the cancer is lung cancer, colon cancer, brain cancer, neuroblastoma, prostate cancer, melanoma, glioblastoma multiform or ovarian cancer. In another embodiment, the cancer is pancreatic cancer, prostate cancer, lung cancer, melanoma, breast cancer, colon cancer, or ovarian cancer. In yet another embodiment, the cancer is breast cancer, colon cancer and ovarian cancer. In yet another embodiment, the cancer is a breast cancer. In yet another embodiment, the cancer is a basal sub-type breast cancer or a luminal B sub-type breast cancer. In yet another embodiment, the cancer is a basal sub-type breast cancer that overexpresses TTK. In yet another embodiment, the basal sub-type breast cancer is ER (estrogen receptor), HER2 and PR (progesterone receptor) negative breast cancer. In yet another embodiment, the cancer is a soft tissue cancer. A "soft tissue cancer" is an art-recognized term that encompasses tumors derived from any soft tissue of the body. Such soft tissue connects, supports, or surrounds various structures and organs of the body, including, but not limited to, smooth muscle, skeletal muscle, tendons, fibrous tissues, fatty tissue, blood and lymph vessels, perivascular tissue, nerves, mesenchymal cells and synovial tissues. Thus, soft tissue cancers can be of fat tissue, muscle tissue, nerve tissue, joint tissue, blood vessels, lymph vessels, and fibrous tissues. Soft tissue cancers can be benign or malignant. Generally, malignant soft tissue cancers are referred to as sarcomas, or soft tissue sarcomas. There are many types of soft tissue tumors, including lipoma, lipoblastoma, hibernoma, liposarcoma, leiomyoma, leiomyosarcoma, rhabdomyoma, rhabdomyosarcoma, neurofibroma, schwannoma (neurilemoma), neuroma, malignant schwannoma, neurofibrosarcoma, neurogenic sarcoma, nodular tenosynovitis, synovial sarcoma, hemangioma, glomus tumor, hemangiopericytoma, hemangioendothelioma, angiosarcoma, Kaposi sarcoma, lymphangioma, fibroma, elastofibroma, superficial fibromatosis, fibrous histiocytoma, fibrosarcoma, fibromatosis, dermatofibrosarcoma protuberans (DFSP), malignant fibrous histiocytoma (MFH), myxoma, granular cell tumor, malignant mesenchymomas, alveolar soft-part sarcoma, epithelioid sarcoma, clear cell sarcoma, and desmoplastic small cell tumor. In a particular embodiment, the soft tissue cancer is a sarcoma selected from the group consisting of a fibrosarcoma, a gastrointestinal sarcoma, a leiomyosarcoma, a dedifferentiated liposarcoma, a pleomorphic liposarcoma, a malignant fibrous histiocytoma, a round cell sarcoma, and a synovial sarcoma.

In some embodiments, the present teachings provide methods of inhibiting the growth of tumor-initiating cells or reducing the likelihood of recurrence of a cancer in a subject who is undergoing an anti-cancer therapy. The method comprises the steps of:

a) assessing the subject to determine whether the cancer is in remission; and b) if the cancer is in remission; then administering to the subject an effective amount of a TTK inhibitor (e.g., a compound represented by Structural Formula (I). If the cancer is not in remission, the method optionally further comprises the step of continuing the anti-cancer therapy until the cancer goes into remission and then the step b) of administering an effective amount of a TTK inhitior (e.g., a compound represented by Structural Formula (I).

As used herein, the term "tumor-initiating cells" or "TICs" refer to cells present within some tumors that possess the ability to self-renew and proliferate. These cells are sometimes called cancer stem cells (CSCs) and may be observed to share certain characteristics with normal stem cells, including a stem cell-like phenotype and function. In some embodiments, TICs are characterized by their ability to form tumors after xenotransplantation in immunodeficient mice.

In some embodiments, the present teachings provide methods of inhibiting the growth of tumor-initiating cells or reducing the likelihood of recurrence of a cancer in a subject whose cancer is in remission comprising administering to the subject an effective amount of a TTK inhibitor (e.g, a compound represented by Structural Formula (I)).

In some embodiments, e.g., where the subject is being treated to reduce the likelihood of recurrence of a cancer, the subject has already been treated with an anti-cancer therapy. Alternatively, the subject has already been treated with an anti-cancer therapy and the subject is in remission.

In some embodiments, the present teachings provide methods of treating a subject with a cancer comprising administering to the subject an effective amount of a compound represented by Structural Formula (I) in combination with an effective anti-cancer therapy. In one embodiment, the cancer is a metastatic cancer. A "metastatic cancer" is a cancer that has spread from its primary site to other parts of the body.

In another embodiment, the present teachings are directed to a method of treating a subject with a drug-resistant cancer. A "drug-resistant cancer" is a cancer that is not responsive to one, two, three, four, five or more drugs that are typically used for the treatment of the cancer. In one embodiment, the drug-resistant cancer is mediated by the growth of tumor-initiating cells.

Suitable methods known in the art can be used for assessing a subject to determine whether the cancer is in remission. For example, the size of the tumor and/or tumor markers, usually proteins associated with tumors, can be monitored to determine the state of the cancer. Size of the tumor can be monitored with imaging devices, such as X-ray, MRI, CAT scans, ultrasound, mammography, PET and the like or via biopsy.

For methods described herein, e.g., coadministration methods, the anti-cancer therapy are selected from the group consisting of surgery, radiation therapy, immunotherapy, endocrine therapy, gene therapy and administration of an anti-cancer agent. Alternatively, the anti-cancer therapy is radiation therapy. In another alternative, the anti-cancer therapy is immunotherapy. In another alternative, the anti-cancer therapy is administration of an anti-cancer agent. In yet another alternative, the anti-cancer therapy is surgery.

Radiation therapy is the use of radiation to kill, destroy or treat the cancers. Exemplary radiation therapy includes, but is not limited to, gamma-radiation, neutron beam radiotherapy, electron beam radiotherapy, proton therapy, brachytherapy, and radioiosotope therapy (i.e., systemic radioactive isotopes therapy), An endocrine therapy is a treatment that adds, blocks or removes hormones. For example, chemotherapeutic agents that can block the production or activity of estrogen have been used for treating breast cancer. In addition, hormonal stimulation of the immune system has been used to treat specific cancers, such as renal cell carcinoma and melanoma. In one embodiment, the endocrine therapy comprises administration of natural hormones, synthetic hormones or other synthetic molecules that may block or increase the production of the body's natural hormones. In another embodiment, the endocrine therapy includes removal of a gland that makes a certain hormone.

As use herein, a gene therapy is the insertion of genes into a subject's cell and biological tissues to treat diseases, such as cancer. Exemplary gene therapy includes, but is not limited to, a germ line gene therapy and a somatic gene therapy.

Immunotherapy (also called biological response modifier therapy, biologic therapy, biotherapy, immune therapy, or biological therapy) is treatment that uses parts of the immune system to fight disease. Immunotherapy can help the immune system recognize cancer cells, or enhance a response against cancer cells. Immunotherapies include active and passive immunotherapies. Active immunotherapies stimulate the body's own immune system while passive immunotherapies generally use immune system components created outside of the body.

Examples of active immunotherapies include, but are not limited to vaccines including cancer vaccines, tumor cell vaccines (autologous or allogeneic), dendritic cell vaccines, antigen vaccines, anti-idiotype vaccines, DNA vaccines, viral vaccines, or Tumor-Infiltrating Lymphocyte (TIL) Vaccine with Interleukin-2 (IL-2) or Lymphokine-Activated Killer (LAK) Cell Therapy.

Examples of passive immunotherapies include but are not limited to monoclonal antibodies and targeted therapies containing toxins. Monoclonal antibodies include naked antibodies and conjugated monoclonal antibodies (also called tagged, labeled, or loaded antibodies). Naked monoclonal antibodies do not have a drug or radioactive material attached whereas conjugated monoclonal antibodies are joined to, for example, a chemotherapy drug (chemolabeled), a radioactive particle (radiolabeled), or a toxin (immunotoxin). Examples of these naked monoclonal antibody drugs include, but are not limited to Rituximab (Rituxan), an antibody against the CD20 antigen used to treat, for example, B cell non-Hodgkin lymphoma; Trastuzumab (Herceptin), an antibody against the HER2 protein used to treat, for example, advanced breast cancer; Alemtuzumab (Campath), an antibody against the CD52 antigen used to treat, for example, B cell chronic lymphocytic leukemia (B-CLL); Cetuximab (Erbitux), an antibody against the EGFR protein used, for example, in combination with irinotecan to treat, for example, advanced colorectal cancer and head and neck cancers; and Bevacizumab (Avastin) which is an antiangiogenesis therapy that works against the VEGF protein and is used, for example, in combination with chemotherapy to treat, for example, metastatic colorectal cancer. Examples of the conjugated monoclonal antibodies include, but are not limited to Radiolabeled antibody Ibritumomab tiuxetan (Zevalin) which delivers radioactivity directly to cancerous B lymphocytes and is used to treat, for example, B cell non-Hodgkin lymphoma; radiolabeled antibody Tositumomab (Bexxar) which is used to treat, for example, certain types of non-Hodgkin lymphoma; and immunotoxin Gemtuzumab ozogamicin (Mylotarg) which contains calicheamicin and is used to treat, for example, acute myelogenous leukemia (AML). BL22 is a conjugated monoclonal antibody for treating, for example, hairy cell leukemia, immunotoxins for treating, for example, leukemias, lymphomas, and brain tumors, and radiolabeled antibodies such as OncoScint for example, for colorectal and ovarian cancers and ProstaScint for example, for prostate cancers.

Further examples of therapeutic antibodies that can be used include, but are not limited to, HERCEPTIN® (Trastuzumab) (Genentech, Calif.) which is a humanized anti-HER2 monoclonal antibody for the treatment of patients with metastatic breast cancer; REOPRO® (abciximab) (Centocor) which is an anti-glycoprotein IIb/IIIa receptor on the platelets for the prevention of clot formation; ZENAPAX® (daclizumab) (Roche Pharmaceuticals, Switzerland) which is an immunosuppressive, humanized anti-CD25 monoclonal antibody for the prevention of acute renal allograft rejection; PANOREX™ which is a murine anti-17-IA cell surface antigen IgG2a antibody (Glaxo Wellcome/Centocor); BEC2 which is a murine anti-idiotype (GD3epitope) IgG antibody (ImClone System); IMC-C225 which is a chimeric anti-EGFR IgG antibody (ImClone System); VITAXIN™ which is a humanized anti-αVβ3 integrin antibody (Applied Molecular Evolution/MedImmune); Campath 1H/LDP-03 which is a humanized anti CD52 IgG1 antibody (Leukosite); Smart M195 which is a humanized anti-CD33 IgG antibody (Protein Design Lab/Kanebo); RITUXAN™ which is a chimeric anti-CD20 IgG1 antibody (IDEC Pharm/Genentech, Roche/Zettyaku); LYMPHOCIDE™ which is a humanized anti-CD22 IgG antibody (Immunomedics); LYMPHOCIDE™ Y-90 (Immunomedics); Lymphoscan (Tc-99m-labeled; radioimaging; Immunomedics); Nuvion (against CD3; Protein Design Labs); CM3 is a humanized anti-ICAM3 antibody (ICOS Pharm); IDEC-114 is a primatied anti-CD80 antibody (IDEC Pharm/Mitsubishi); ZEVALIN™ is a radiolabelled murine anti-CD20 antibody (IDEC/Schering AG); IDEC-131 is a humanized anti-CD40L antibody (IDEC/Eisai); IDEC-151 is a primatized anti-CD4 antibody (IDEC); IDEC-152 is a primatized anti-CD23 antibody (IDEC/Seikagaku); SMART anti-CD3 is a humanized anti-CD3 IgG (Protein Design Lab); 5G1.1 is a humanized anti-complement factor 5 (C5) antibody (Alexion Pharm); D2E7 is a humanized anti-TNF-α antibody (CAT/BASF); CDP870 is a humanized anti-TNF-α Fab fragment (Celltech); IDEC-151 is a primatized anti-CD4 IgG1 antibody (IDEC Pharm/SmithKline Beecham); MDX-CD4 is a human anti-CD4 IgG antibody (Medarex/Eisai/Genmab); CD20-sreptdavidin (+biotin-yttrium 90; NeoRx); CDP571 is a humanized anti-TNF-α IgG4 antibody (Celltech); LDP-02 is a humanized anti-α4β7 antibody (LeukoSite/Genentech); OrthoClone OKT4A is a humanized anti-CD4 IgG antibody (Ortho Biotech); ANTOVA™ is a humanized anti-CD40L IgG antibody (Biogen); ANTEGREN™ is a humanized anti-VLA-4 IgG antibody (Elan); and CAT-152 is a human anti-TGF-β$_2$ antibody (Cambridge Ab Tech).

Immunotherapies that can be used in the present teachings include adjuvant immunotherapies. Examples include cytokines, such as granulocyte-macrophage colony-stimulating factor (GM-CSF), granulocyte-colony stimulating factor (G-CSF), macrophage inflammatory protein (MIP)-1-alpha, interleukins (including IL-1, IL-2, IL-4, IL-6,IL-7, IL-12, IL-15, IL-18, IL-21, and IL-27), tumor necrosis factors (including TNF-alpha), and interferons (including IFN-alpha, IFN-beta, and IFN-gamma); aluminum hydroxide (alum); Bacille Calmette-Guérin (BCG); Keyhole limpet hemocyanin (KLH); Incomplete Freund's adjuvant (IFA); QS-21; DETOX; Levamisole; and Dinitrophenyl (DNP), and combinations thereof, such as, for example, combinations of, interleukins, for example, IL-2 with other cytokines, such as IFN-alpha.

Alternatively, the anti-cancer therapy described herein includes administration of an anti-cancer agent. An "anti-cancer agent" is a compound, which when administered in an effective amount to a subject with cancer, can achieve, partially or substantially, one or more of the following: arresting the growth, reducing the extent of a cancer (e.g., reducing size of a tumor), inhibiting the growth rate of a cancer, and ameliorating or improving a clinical symptom or indicator associated with a cancer (such as tissue or serum components) or increasing longevity of the subject.

The anti-cancer agent suitable for use in the methods described herein includes any anti-cancer agents that have been approved for the treatment of cancer. In one embodiment, the anti-cancer agent includes, but is not limited to, a targeted antibody, an angiogenesis inhibitor, an alkylating agent, an antimetabolite, a vinca alkaloid, a taxane, a podophyllotoxin, a topoisomerase inhibitor, a hormonal antineoplastic agent and other antineoplastic agents.

Examples of alkylating agents useful in the methods of the present teachings include but are not limited to, nitrogen mustards (e.g., mechloroethamine, cyclophosphamide, chlorambucil, melphalan, etc.), ethylenimine and methylmelamines (e.g., hexamethylmelamine, thiotepa), alkyl sulfonates (e.g., busulfan), nitrosoureas (e.g., carmustine, lomusitne, semustine, streptozocin, etc.), or triazenes (decarbazine, etc.). Examples of antimetabolites useful in the methods of the present teachings include but are not limited to folic acid analog (e.g., methotrexate), or pyrimidine analogs (e.g., fluorouracil, floxouridine, Cytarabine), purine analogs (e.g., mercaptopurine, thioguanine, pentostatin). Examples of plant alkaloids and terpenoids or derivatives thereof include, but are not limited to, vinca alkaloids (e.g., vincristine, vinblastine, vinorelbine, vindesine), podophyllotoxin, and taxanes (e.g., paclitaxel, docetaxel). Examples of a topoisomerase inhibitor include, but are not limited to, irinotecan, topotecan, amsacrine, etoposide, etoposide phosphate and teniposide. Examples of antineoplastic agents include, but are not limited to, actinomycin, anthracyclines (e.g., doxorubicin, daunorubicin, valrubicin, idarubicin, epirubicin), bleomycin, plicamycin and mitomycin.

In one embodiment, the anti-cancer agents that can be used in the present teachings include Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Yet other anti-cancer agents/drugs that can be used in the present teachings include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-aminotriazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine octfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer. Preferred additional anti-cancer drugs are 5-fluorouracil and leucovorin.

In one embodiment, the anti-cancer agents that can be used in methods described herein are selected from the group consisting of paclitaxel, docetaxel, 5-fluorouracil, trastuzumab, lapatinib, bevacizumab, letrozole, goserelin, tamoxifen, cetuximab, panitumumab, gemcitabine, capecitabine, irinotecan, oxaliplatin, carboplatin, cisplatin, doxorubicin, epirubicin, cyclophosphamide, methotrexate, vinblastine, vincristine, melphalan and a combination thereof.

In one embodiment, the anti-cancer agent and the compound represented by Structural Formula (I) are administered contemporaneously. When administered contemporaneously, the anti-cancer agent and the compound can be administered in the same formulation or in different formulations. Alternatively, the compound and the additional anti-cancer agent are administered separately. Alternatively, the compound and the additional anti-cancer agent can be administered sequentially, as separate compositions, within an appropriate time frame (e.g., a cancer treatment session/interval (e.g., about 1.5 to about 5 hours to about 10 hours to about 15 hours to about 20 hours; about 1 day to about 2 days to about 5 days to about 10 days to about 14 days)) as determined by the skilled clinician (e.g., a time sufficient to allow an overlap of the pharmaceutical effects of the therapies). The compound and the additional anti-cancer agent can be administered in a single dose or multiple doses in an order and on a schedule suitable to achieve a desired therapeutic effect (e.g., inhibition of tumor growth).

In one embodiment, the subject in the methods described herein has not been previously treated with a TTK inhibitor (e.g., the compound represented by Structural Formula (I).

The term "inhibiting the growth of tumor-initiating cells" refers to decreasing the rate of the proliferation and/or survival of the tumor-initiating cells.

As used herein, the term "reducing the likelihood of recurrence of a cancer" means partially or totally inhibiting, delaying the return of a cancer at or near a primary site and/or at a secondary site after a period of remission. It also means that the cancer is less likely to return with treatment described herein than in its absence.

As used herein, the term "remission" refers to a state of cancer, wherein the clinical symptoms or indicators associated with a cancer have disappeared or cannot be detected, typically after the subject has been successfully treated with an anti-cancer therapy.

As used herein, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e., not worsening) state of disease, reducing the likelihood of the spread of the disease, delay or slowing of disease progression, amelioration or palliation of the disease state, whether detectable or undetectable. "Treatment" can also mean prolonging survival as compared to expected survival if not receiving treatment. "Treatment" also includes reducing the likelihood of reoccurrence of the disease.

As used herein, "treating a subject with a cancer" includes achieving, partially or substantially, one or more of the following: arresting the growth, reducing the extent of the cancer (e.g., reducing size of a tumor), inhibiting the growth rate of the cancer, ameliorating or improving a clinical symptom or indicator associated with the cancer (such as tissue or serum components) or increasing longevity of the subject; and reducing the likelihood of recurrence of the cancer.

Generally, an effective amount of a compound taught herein varies depending upon various factors, such as the given drug or compound, the pharmaceutical formulation, the route of administration, the type of disease or disorder, the identity of the subject or host being treated, and the like, but can nevertheless be routinely determined by one skilled in the art. An effective amount of a compound of the present teachings may be readily determined by one of ordinary skill by routine methods known in the art.

The term an "effective amount" means an amount when administered to the subject which results in beneficial or desired results, including clinical results, e.g., inhibits, suppresses or reduces the cancer (e.g., as determined by clinical symptoms or the amount of cancer cells) in a subject as compared to a control.

In an embodiment, an effective amount of a compound taught herein ranges from about 0.1 to about 1000 mg/kg body weight, alternatively about 1 to about 500 mg/kg body weight, and in another alternative, from about 20 to about 300 mg/kg body weight. In another embodiment, an effective amount of a compound taught herein ranges from about 0.5 to about 5000 mg/m$^2$, alternatively about from 5 to about 2500 mg/m$^2$, and in another alternative from about 50 to about 1000 mg/m$^2$. The skilled artisan will appreciate that certain factors may influence the dosage required to effectively treat a subject suffering from cancer or reduce the likelihood of recurrence of a cancer. These factors include, but are not limited to, the severity of the disease or disorder, previous treatments, the general health and/or age of the subject and other diseases present.

Moreover, for methods described herein (including treating a subject with a cancer or reducing the likelihood of recurrence of a cancer), a "treatment" or dosing regimen of a subject with an effective amount of the compound of the present teachings may consist of a single administration, or alternatively comprise a series of applications. For example, the compound of the present teachings may be administered at least once a week. However, in another embodiment, the compound may be administered to the subject from about one time per week to once daily for a given treatment. The length of the treatment period depends on a variety of factors, such as the severity of the disease, the age of the patient, the concentration and the activity of the compounds of the present teachings, or a combination thereof. It will also be appreciated that the effective dosage of the compound used for the treatment may increase or decrease over the course of a particular treatment regime. Changes in dosage may result and become apparent by standard diagnostic assays known in the art. In some instances, chronic administration may be required.

A "subject" is a mammal, preferably a human, but can also be an animal in need of veterinary treatment, e.g., companion animals (e.g., dogs, cats, and the like), farm animals (e.g., cows, sheep, pigs, horses, and the like) and laboratory animals (e.g., rats, mice, guinea pigs, and the like).

The compounds taught herein can be administered to a patient in a variety of forms depending on the selected route of administration, as will be understood by those skilled in the art. The compounds of the present teachings may be administered, for example, by oral, parenteral, buccal, sublingual, nasal, rectal, patch, pump or transdermal administration and the pharmaceutical compositions formulated accordingly. Parenteral administration includes intravenous, intraperitoneal, subcutaneous, intramuscular, transepithelial, nasal, intrapulmonary, intrathecal, rectal and topical modes of administration. Parenteral administration can be by continuous infusion over a selected period of time.

The compounds taught herein can be suitably formulated into pharmaceutical compositions for administration to a subject. The pharmaceutical compositions of the present teachings optionally include one or more pharmaceutically acceptable carriers and/or diluents therefor, such as lactose, starch, cellulose and dextrose. Other excipients, such as flavoring agents; sweeteners; and preservatives, such as methyl, ethyl, propyl and butyl parabens, can also be included. More complete listings of suitable excipients can be found in the Handbook of Pharmaceutical Excipients (5$^{th}$ Ed., Pharmaceutical Press (2005)). A person skilled in the art would know how to prepare formulations suitable for various types of administration routes. Conventional procedures and ingredients for the selection and preparation of suitable formulations are described, for example, in Remington's Pharmaceutical Sciences (2003-20th edition) and in The United States Pharmacopeia: The National Formulary (USP 24 NF19) published in 1999. The carriers, diluents and/or excipients are "acceptable" in the sense of being compatible with the other ingredients of the pharmaceutical composition and not deleterious to the recipient thereof.

Typically, for oral therapeutic administration, a compound of the present teachings may be incorporated with excipient and used in the form of ingestible tablets, buccal tablets, troches, capsules, elixirs, suspensions, syrups, wafers, and the like.

Typically for parenteral administration, solutions of a compound of the present teachings can generally be prepared in water suitably mixed with a surfactant such as hydroxypropylcellulose. Dispersions can also be prepared in glycerol, liquid polyethylene glycols, DMSO and mixtures thereof with or without alcohol, and in oils. Under ordinary conditions of storage and use, these preparations contain a preservative to prevent the growth of microorganisms.

Typically, for injectable use, sterile aqueous solutions or dispersion of, and sterile powders of, a compound described herein for the extemporaneous preparation of sterile injectable solutions or dispersions are appropriate.

For nasal administration, the compounds of the present teachings can be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomizing device. Alternatively, the sealed container may be a unitary dispensing device such as a single dose nasal inhaler or an aerosol dispenser fitted with a metering valve which is intended for disposal after use. Where the dosage form comprises an aerosol dispenser, it will contain a propellant which can be a compressed gas such as compressed air or an organic propellant such as fluorochlorohydrocarbon. The aerosol dosage forms can also take the form of a pump-atomizer.

For buccal or sublingual administration, the compounds of the present teachings can be formulated with a carrier such as sugar, acacia, tragacanth, or gelatin and glycerine, as tablets, lozenges or pastilles.

For rectal administration, the compounds described herein can be formulated in the form of suppositories containing a conventional suppository base such as cocoa butter.

The compounds of invention may be prepared by methods known to those skilled in the art, as illustrated by the general schemes and procedures below and by the preparative examples that follow. All starting materials are either commercially available or prepared by methods known to those skilled in the art and the procedures described below.

In accordance with another aspect of the present invention, the compounds of the invention can be prepared by processes analogues to those established in the art. General methods to synthesize the claimed compounds are elaborated below in Example A.

EXEMPLIFICATION

Example A

Synthesis

General Methods

Commercially available starting materials, reagents, and solvents were used as received. In general, anhydrous reactions were performed under an inert atmosphere such as nitrogen or Argon. PoraPak® Rxn CX refers to a commercial cation-exchange resin available from Waters.

Microwave reactions were performed with a Biotage Initiator microwave reactor. Reaction progress was generally monitored by TLC using Merck silica gel plates with visualization by UV at 254 nm, by analytical HPLC or by LCMS (Bruker Exquire 4000 or Waters Acquity UPLC system). Flash column chromatographic purification of intermediates or final products was performed using 230-400 mesh silica gel 60 from EMD chemicals or Silicycle, or purified using a Biotage Isolera with KP-SIL or HP-SIL silica cartridges, or KP-NH basic modified silica and corresponding samplets. Reverse-phase HPLC purification was performed on a Varian PrepStar model SD-1 HPLC system with a Varian Monochrom 10μ C-18 reverse-phase column using a of about 5-30% MeCN or MeOH/0.05% TFA-H$_2$O to 70-90% MeCN or MeOH/0.05% TFA in H$_2$O over a 20-40-min period at a flow rate of 30-80 mL/min. Reverse phase purification was also performed using a Biotage Isolera equipped with a KP-C18-H column using a between 10-95% MeOH or CH3CN/0.1% TFA in H$_2$O. Proton NMRs were recorded on a Bruker 400 MHz spectrometer, and mass spectra were obtained using a Bruker Esquire 4000 spectrometer or Waters Acquity UPLC system.

Compound names were generated using the software built into CambridgeSoft-PerkinElmer's ChemBioDraw Ultra version 11.0 or 12.0.

Abbreviations:
aq aqueous
Ar argon
Boc tert-butoxycarbonyl
br. broad
calcd calculated d doublet
DCM dichloromethane
DIPEA diisopropylethylamine
DMF N,N-dimethylformamide
DMSO dimethylsulfoxide
dppf 1,1+-bis( diphenylphosphino) ferrocene
h hour
HPLC high performance liquid chromatography
LC-MS liquid chromatography coupled to mass spectrometry
min minute
m multiplet
MS ESI mass spectra, electrospray ionization
NMR nuclear magnetic resonance
O/N overnight
PE petroleum ether
PMB para-methoxybenzyl
prep preparative
rt room temperature
s singlet
t triplet
TFA trifluoroacetic acid
THF tetrahydrofuran

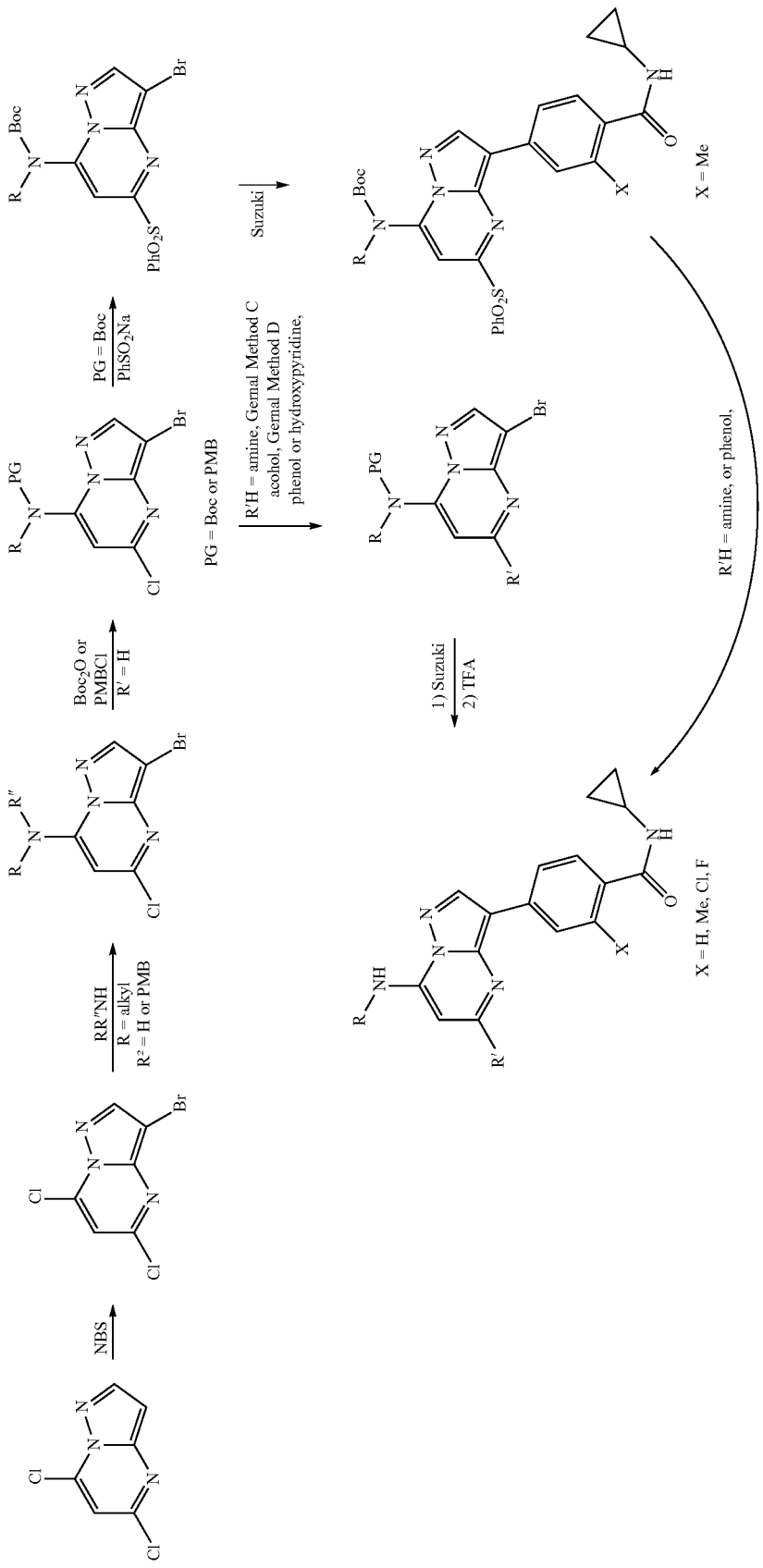

Intermediates

4-bromo-N-cyclopropyl-2-methylbenzamide

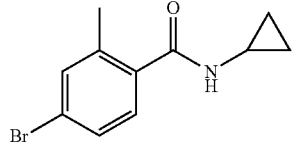

To a suspension of 4-bromo-2-methylbenzoic acid (43.0 g, 200 mmol) and oxalyl dichloride (30.5 g, 240 mmol) in DCM (300 mL) was added DMF (0.1 mL). The resulting reaction mixture was stirred at rt for 16 h. The reaction turned into a clear yellow solution slowly over 16 h. Solvent was then removed in vacuo, and the crude product was used in the next step without further purification. The crude product was redissolved in DCM (300 mL) and cooled to 0° C. A mixture of TEA (42 mL, 300 mmol) and cyclopropylamine (12.6 g, 220 mmol) in DCM (100 mL) was added slowly over 15 min, and the resulting mixture was stirred at rt for 2 h. The reaction was diluted with DCM (200 mL) and water was added. The resulting mixture was extracted with DCM and the combined organic extracts were dried over MgSO$_4$ and concentrated to give the desired product as a pale pink solid (50.1 g, 99%). $^1$H NMR (400 MHz, CDCl$_3$) δ ppm 7.37 (s, 1H), 7.31 (d, J=8.0 Hz, 1H), 7.17 (d, J=8.1 Hz, 1H), 5.93 (br. s, 1H), 2.90-2.85 (m, 1H), 2.40 (s, 3H), 0.90-0.85 (m, 2H), 0.62-0.58 (m, 2H); MS ESI [M+H]$^+$ 253.9, calcd for [C$_{11}$H$_{12}$BrNO+H]$^+$ 254.0.

N-(4-bromo-2-methylphenyl)cyclopropanecarboxamide

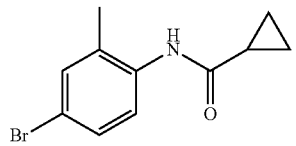

In a 100 mL RBF, 4-bromo-2-methylaniline (3.7 g, 20 mmol) and DIPEA (6.95 mL, 40 mmol) were combined with DMF (40 mL). The reaction was cooled to 0° C. in an ice bath and cyclopropanecarbonyl chloride (2.1 g, 20 mmol) was added. The mixture was stirred at 0° C for 1 h. Water and EtOAc were added to separate the phases and the aqueous phase was extracted with EtOAc. The organic layers were combined, dried over Na$_2$SO$_4$, filtered, and concentrated under reduced pressure to give the title compound as a white solid (4.76 g, 94%). $^1$H NMR (400 MHz, CDCl$_3$) δ ppm 7.85-7.72 (m, 1H), 7.38-7.28 (m, 2H), 7.15-7.02 (m, 1H), 2.27 (s, 3H), 1.57-1.48 (m, 1H), 1.10 (quint, J=3.9 Hz, 2H), 0.92-0.79 (m, 2H); MS ESI [M+H]$^+$ 253.9, calcd for [C$_{11}$H$_{12}$BrNO+H]$^+$ 254.0.

N-cyclopropyl-2-methyl-4-(4,4,5,5-tetramethyl-1,3,2-dioxaborolan-2-yl)benzamide

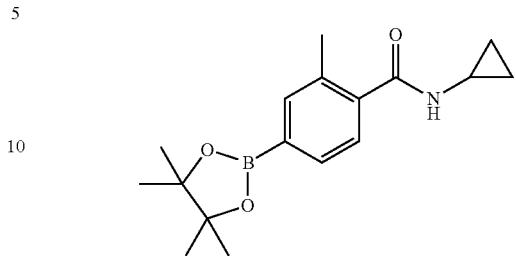

To a mixture of 4-bromo-N-cyclopropyl-2-methylbenzamide (3.73 g, 14 mmol), Bis(pinacolato)diboron (5.59 g, 22 mmol), and KOAc (4.29 g, 43 mmol) in DMF (37 mL) was purged with Ar for 10 min at rt. Then PdCl$_2$(dppf)·DCM (0.59 g, 5 mol %) was added and the reaction was heated at 100° C. in oil bath for 4 h. After reaction completion the reaction mass was diluted with EtOAc (200 mL) and H$_2$O (100 mL). The combined layer filtered through celite pad and washed it with little EtOAc. The aq. layer further extracted with EtOAc (50 mL) and the combined organic layer washed with brine, dried over Na$_2$SO$_4$, filtered, and concentrated to give crude oily residue. The crude product was purified by flash chromatography (gradient: EtOAc/hex 0-100%) to give the title compound as a creamy solid (4.15 g, 94%). $^1$H NMR (400 MHz, CDCl$_3$) δ ppm 7.66 (s, 1H), 7.63-7.61 (d, J=7.6 Hz, 1 H), 7.32-7.30 (d, J=7.6 Hz, 1H), 5.85 (s, 1 H), 2.93-2.87 (m, 1H), 2.46 (s, 3H), 1.35 (s, 12H), 0.90-0.86 (m, 2H), 0.63-0.59 (m, 2H); MS ESI [M+H]$^+$ 302.2, calcd for [C$_{17}$H$_{24}$BNO$_3$+H]$^+$ 302.2.

3-bromo-5,7-dichloropyrazolo[1,5-a]pyrimidine

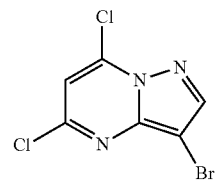 [SMILES: Clc1cc(Cl)n2ncc(Br)c2n1]

To a stirred solution of sodium ethoxide in EtOH, which was prepared from sodium (281.3 g, 12.0 mol) and EtOH (10 L) by the conventional method, were added diethyl malonate (963.7 g, 6.02 mol) at ambient temperature and then compound 1H-pyrazol-3-amine (500 g, 6.02 mol).

The reaction mixture was refluxed for 12 hours. After cooled to room temperature, the precipitates were collected by filtration and dissolved in water. The aqueous solution was acidified with 2 M HCl (pH=2). The resulting precipitates were collected by filtration and dried under reduced pressure to afford pyrazolo[1,5-a]pyrimidine-5,7(4H,6H)-dione (649 g, 71%) as a yellow solid, which was used for the next reaction without further purification.

A stirred suspension of pyrazolo[1,5-a]pyrimidine-5,7 (4H,6H)-dione (265 g, 1.75 mol) and N,N-dimethylaniline (335.6 mL) in POCl$_3$ (2.00 kg, 13.2 mol) was refluxed for 4 hours. After cooled to room temperature, the reaction mixture was poured into ice-water, and stirred for 30 min, neutralized with saturated aqueous sodium carbonate and extracted with EtOAc. The combined organic layers were washed with water, brine and dried over MgSO$_4$, filtered and evaporated. The residue was purified by column chromatography on silica gel (gradient: EtOAc/PE 1:10) to give 5,7-dichloropyrazolo[1,5-a]pyrimidine (287 g, 87%) as a yellow solid.

To a solution 5,7-dichloropyrazolo[1,5-a]pyrimidine (246.6 g, 1.31 mol) in CH$_3$CN (1.8 L) was added NBS (245 g, 1.38 mol). The resulting mixture was stirred at room temperature for 2 hours. After removal of the solution, the reaction mixture was purified by column chromatography on silica gel (gradient: EtOAc/PE 1:5) to give the title compound (313.5 g, 89%) as light yellow solid. $^1$H NMR (300 MHz, CDCl$_3$): δ ppm 7.04 (s, 1H), 8.21 (s, 1H); MS ESI [M+H]$^+$ 265.9, calcd for [C$_6$H$_2$BrCl$_2$N$_3$+H]$^+$ 265.9.

3-bromo-5-chloro-N-(cyclopropylmethyl)pyrazolo [1,5-a]pyrimidin-7-amine

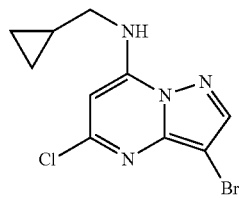 [SMILES: Clc1cc(NCC2CC2)n2ncc(Br)c2n1]

To a solution of 3-bromo-5,7-dichloropyrazolo[1,5-a]pyrimidine (5.0 g, 19 mmol) in DCM (50 mL) was added cyclopropylmethanamine (1.48 g, 21 mmol), and DIPEA (6.6 mL, 38 mmol). The reaction was stirred at rt for 2 h. Water and DCM were added to separate the phases and the aqueous phase was extracted with DCM. The combined organic extracts were dried over NaSO$_4$, filtered and concentrated. The crude product was purified by flash chromatography (gradient: EtOAc/hex 0-50%) to give the title compound as a yellow solid (5.25 g, 92%). $^1$H NMR (400 MHz, CDCl$_3$) δ ppm 7.97 (s, 1H), 6.50 (br. s, 1H), 5.97 (s, 1H), 3.25 (dd, J=7.3, 5.5 Hz, 2H), 1.26-1.13 (m, 1H), 0.74-0.65 (m, 2H), 0.37 (q, J=5.0 Hz, 2H); MS ESI [M+H]$^+$ 301.0, calcd for [C$_{10}$H$_{10}$BrClN$_4$+H]$^+$ 301.0.

(1s,3s)-3-(((3-bromo-5-chloropyrazolo[1,5-a]pyrimidin-7-yl)amino)methyl)-1-methylcyclobutanol

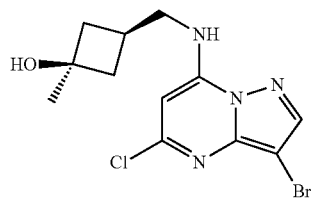 [SMILES: C[C@]1(O)C[C@@H](CNc2cc(Cl)nc3c(Br)cnn23)C1]

To a solution of 3-bromo-5,7-dichloropyrazolo[1,5-a]pyrimidine (14.6 g, 55.3 mmol) in DCM (200 mL) was added cis-hydroxy-3-methylcyclobutane-1-methylamine (7.0 g, 60.9 mmol), and DIPEA (19.2 mL, 110.6 mmol). The reaction was stirred at rt for 16 h. Water and DCM were added to separate the phases and the aqueous phase was extracted with DCM. The combined organic extracts were dried over Na$_2$SO$_4$, filtered and concentrated to give the title compound as a yellow solid (18.1 g, 95%). $^1$H NMR (400 MHz, CDCl$_3$) δ ppm 7.96 (s, 1 H), 6.60-6.49 (m, 1H), 5.99 (s, 1H), 3.47 (t, J=6.0 Hz, 2H), 2.38-2.27 (m, 3H), 1.96-1.85 (m, 2H), 1.43 (s, 3H); MS ESI [M+H]$^+$ 345.1, calcd for [C$_{12}$H$_{14}$BrClN$_4$O+H]$^+$ 345.0.

tert-butyl (3-bromo-5-chloropyrazolo[1,5-a]pyrimidin-7-yl)(cyclopropylmethyl)carbamate

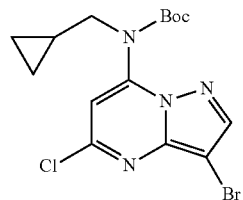 [SMILES: CC(C)(C)OC(=O)N(CC1CC1)c1cc(Cl)nc2c(Br)cnn12]

To a solution of 3-bromo-5-chloro-N-(cyclopropylmethyl)pyrazolo[1,5-a]pyrimidin-7-amine (5.25 g, 17.5 mmol) in DCM (150 mL) was added Boc$_2$O (5.70 g, 26.2 mmol), DMAP (0.21 g, 1.75 mmol), and TEA (7.3 mL, 52.5 mmol). The reaction was stirred at rt for 4 h. Water and DCM were added to separate the phases and the aqueous phase was extracted with DCM. The combined organic extracts were dried over MgSO$_4$, filtered and concentrated. The crude product was purified by flash chromatography (gradient: EtOAc/hex 0-40%) to give the title compound as a yellow solid (6.24 g, 89%). $^1$H NMR (400 MHz, CDCl$_3$) δ ppm 8.12 (s, 1H), 6.85 (s, 1H), 3.72 (d, J=7.3 Hz, 2H), 1.39 (s, 9H), 1.05-0.94 (m, 1H), 0.46-0.37 (m, 2H), 0.13-0.03 (m, 2H); MS ESI [M-C$_4$H$_8$]$^+$ 345.0, calcd for [C$_{15}$H$_8$BrClN$_4$O$_2$-C$_4$H$_8$]$^+$ 345.0.

tert-butyl (3-bromo-5-chloropyrazolo[1,5-a]pyrimidin-7-yl)(((1s,3s)-3-((tert-butoxycarbonyl)oxy)-3-methylcyclobutyl)methyl)carbamate

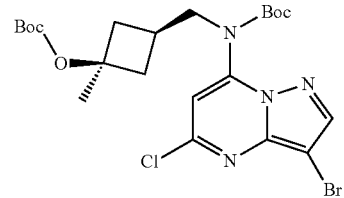 [SMILES: CC(C)(C)OC(=O)O[C@]1(C)C[C@H](CN(C(=O)OC(C)(C)C)c2cc(Cl)nc3c(Br)cnn23)C1]

To a solution of (1s,3s)-3-(((3-bromo-5-chloropyrazolo[1,5-a]pyrimidin-7-yl)amino)methyl)-1-methylcyclobutanol (18.1 g, 52.6 mmol), Boc$_2$O (34.3 g, 158 mmol), and ), and TEA (22 mL, 157.8 mmol) in DCM (200 mL) was added DMAP (1.28 g, 10.5 mmol). The reaction was stirred at 40° C. for 16 h. The solvent was removed in vacuo and water and DCM were added to separate the phases and the aqueous phase was extracted with DCM. The combined organic extracts were dried over NaSO$_4$, filtered and concentrated. The crude product was purified by flash chromatography (3 Biotage 100 g SiO$_2$ columns in parallel, gradient: EtOAc/hex 0-30%) to give the title compound as a beige solid (12.7 g, 44%). $^1$H NMR (400 MHz, CDCl$_3$) δ ppm 8.11 (s, 1H), 6.74 (s, 1H), 3.88 (d, J=6.5 Hz, 2H), 2.17 (s, 3H), 1.99-1.88 (m, 2H), 1.47 (s, 3H), 1.45 (s, 9H), 1.35 (s, 9H); MS ESI [M+H]$^+$ 545.1, calcd for [C$_{22}$H$_{30}$BrClN$_4$O$_5$+H]$^+$ 545.1.

(1s,3s)-3-(((3-bromo-5-chloropyrazolo[1,5-a]pyrimidin-7-yl)(4-methoxybenzyl)amino)methyl)-1-methylcyclobutanol

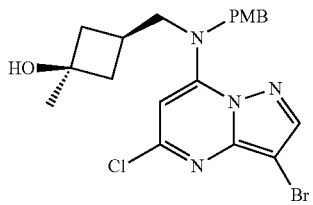

To a solution of (1s,3s)-3-(((3-bromo-5-chloropyrazolo[1,5-a]pyrimidin-7-yl)amino)methyl)-1-methylcyclobutanol (12.0 g, 34.7 mmol) and 4-methoxybenzyl chloride (5.2 mL, 38.2 mmol) in DMF (50 mL) was added $K_2CO_3$ (9.6 g, 69.4 mmol). The resulting mixture was stirred at 60° C. for 3 h. Water and EtOAc were added to separate the phases and the aqueous phase was extracted with EtOAc. The combined organic extracts were washed with water, dried over $MgSO_4$, filtered and concentrated. The crude product was purified by flash chromatography (gradient: EtOAc/hex 10-100%) using three columns in parallel. Impure fractions were collected and purified by flash chromatography using the above conditions. Pure fractions were combined and concentrated to give the desired product as a pale yellow solid (13.1 g, 81%). $^1$H NMR (400 MHz, $CDCl_3$) δ ppm 8.01 (s, 1H), 7.17 (d, J=8.7 Hz, 2H), 6.67 (d, J=8.7 Hz, 2H), 6.02 (s, 1H), 4.98 (s, 2H), 3.83 (d, J=6.4 Hz, 2H), 3.81 (s, 3H), 2.25-2.16 (m, 3H), 1.76-1.72 (m, 2H), 1.36 (s, 3H); MS ESI [M+H]$^+$ 467.1, calcd for $[C_{20}H_{22}BrClN_4O_2+H]^+$ 467.1.

tert-butyl (3-bromo-5-(((1S,2R)-2-hydroxycyclohexyl)amino)pyrazolo[1,5-a]pyrimidin-7-yl)(cyclopropylmethyl)carbamate

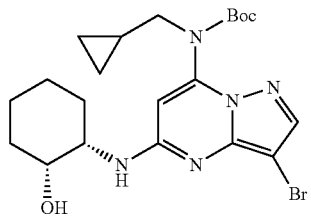 [SMILES: CC(C)(C)OC(=O)N(CC1CC1)c1cc(N[C@H]2CCCC[C@H]2O)nc2c(Br)cnn12]

To a solution of using tert-butyl (3-bromo-5-chloropyrazolo[1,5-a]pyrimidin-7-yl)(cyclopropylmethyl)carbamate (9.0 g, 22.5 mmol) in NMP (90 mL) was added (1R,2S)-2-aminocyclohexanol·HCl (4.08 g, 27.0 mmol), and DIPEA (3.47 g, 25.1 mmol). The reaction was divided and sealed into six microwave vials. Each vial was microwaved for 3 h at 130° C. Water and EtOAc were added to separate the phases and the aqueous phase was extracted with EtOAc. The combined organic extracts were dried over $Na_2SO_4$, filtered and concentrated. The crude product was purified by flash chromatography (gradient: EtOAc/hex 0-50%) using three columns in parallel to give the title compound as a beige solid (8.51 g, 79%). $^1$H NMR (400 MHz, $CDCl_3$) δ ppm 7.80 (s, 1H), 6.08 (s, 1H), 5.33-5.19 (m, 1H), 4.26-4.14 (m, 1H), 4.13-4.06 (m, 1H), 3.61 (d, J=7.3 Hz, 2H), 2.51 (br. s, 1H), 1.89-1.62 (m, 8H), 1.55-1.45 (m, 2H), 1.40 (s, 9H), 1.06-0.95 (m, 1H), 0.47-0.38 (m, 2H), 0.17-0.07 (m, 2H); MS ESI [M+H]$^+$ 408.3, calcd for $[C_{21}H_{30}BrN_5O_3+H]^+$ 480.2.

tert-butyl (3-bromo-5-(pyridin-3-yloxy)pyrazolo[1,5-a]pyrimidin-7-yl)(cyclopropylmethyl)carbamate

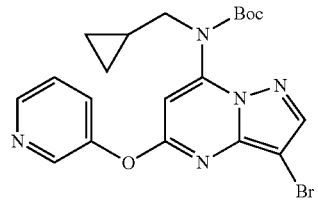 [SMILES: CC(C)(C)OC(=O)N(CC1CC1)c1cc(Oc2cccnc2)nc2c(Br)cnn12]

A mixture of tert-butyl (3-bromo-5-chloropyrazolo[1,5-a]pyrimidin-7-yl)(cyclopropylmethyl)carbamate (400 mg, 1.0 mmol), 3-hydroxypyridine (475 mg, 5.0 mmol), DBU (0.75 mL, 5.0 mmol) in DME (5 mL) was combined and sealed into a microwave vial. The mixture was microwaved for 1 h at 85° C. Water and EtOAc were added to separate the phases and the aqueous phase was extracted with EtOAc. The combined organic extracts were dried over $Na_2SO_4$, filtered and concentrated. The crude product was purified by flash chromatography (gradient: EtOAc/hex 0-50%) to give the title compound as a brown oil (367 mg, 80%). $^1$H NMR (400 MHz, $CDCl_3$) δ ppm 8.64 (d, J=2.5 Hz, 1H) 8.54 (dd, J=4.5, 1.5 Hz, 1H) 7.97 (s, 1H), 7.78-7.72 (m, 1H), 7.44-7.38 (m, 1H) 6.61 (s, 1H) 3.71 (d, J=7.3 Hz, 2H) 1.39 (s, 9 H), 1.06-1.01 (m, 1H) 0.45 (s, 2H), 0.13-0.09 (m, 2H); MS ESI [M+H]$^-$ 460.0, calcd for $[C_{20}H_{22}BrN_5O_3+H]^+$ 460.1.

tert-butyl (3-bromo-5-(cyclopentylamino)pyrazolo[1,5-a]pyrimidin-7-yl)(((1s,3s)-3-((tert-butoxycarbonyl)oxy)-3-methylcyclobutyl)methyl)carbamate

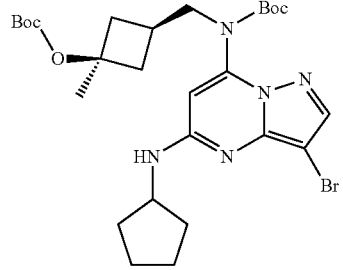 [SMILES: CC(C)(C)OC(=O)O[C@]1(C)C[C@H](CN(C(=O)OC(C)(C)C)c2cc(NC3CCCC3)nc3c(Br)cnn23)C1]

To a solution of tert-butyl (3-bromo-5-chloropyrazolo[1,5-a]pyrimidin-7-yl)(((1s,3s)-3-((tert-butoxycarbonyl)oxy)-3-methylcyclobutyl)methyl)carbamate (0.45 g, 0.83 mmol) in NMP (4 mL) was added cyclopentylamine (0.085 g, 1.0 mmol), and DIPEA (0.21 g, 1.66 mmol). The reaction was microwaved for 3 h at 130° C. Water and EtOAc were added to separate the phases and the aqueous phase was extracted with EtOAc. The combined organic extracts were dried over $Na_2SO_4$, filtered and concentrated. The crude product was purified by flash chromatography (gradient: EtOAc/hex 0-60%) to give the title compound as a white solid (0.40 g, 67%). $^1$H NMR (400 MHz, $CDCl_3$) δ ppm 7.79 (s, 1H), 5.94 (s, 1H), 5.08 (br. s, 1H), 4.23 (br. s, 1H), 3.85-3.72 (m, 2H), 2.28-2.06 (m, 5H), 2.02-1.89 (m, 2H), 1.81-1.61 (m, 5H), 1.48 (s, 4H), 1.44 (s, 9H), 1.36 (s, 9H); MS ESI [M+H]+ 594.3, calcd for [C27H40BrN5O5+H]+ 594.2.

tert-butyl (3-bromo-5-(pyridin-3-yloxy)pyrazolo[1,5-a]pyrimidin-7-yl)(((1s,3s)-3-((tert-butoxycarbonyl)oxy)-3-methylcyclobutyl)methyl)carbamate

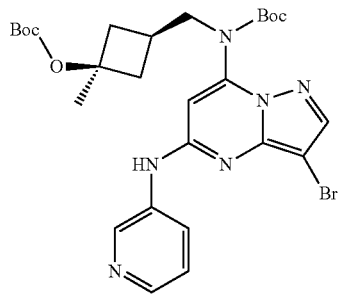 [SMILES: CC(C)(C)OC(=O)O[C@]1(C)C[C@H](CN(C(=O)OC(C)(C)C)c2cc(Nc3cccnc3)nc3c(Br)cnn23)C1]

A mixture of tert-butyl (3-bromo-5-chloropyrazolo[1,5-a]pyrimidin-7-yl)(((1s,3s)-3-((tert-butoxycarbonyl)oxy)-3-methylcyclobutyl)methyl)carbamate (12.7 g, 23.3 mmol), 3-hydroxypyridine (4.43 g, 46.6 mmol), and K2CO3 (9.65 g, 69.9 mmol) was combined in DMF (100 mL) and stirred at rt overnight. The reaction mixture was diluted with EtOAc and washed with water, dried over Na2SO4, filtered and concentrated in vacuo. The crude product was triturated with Et2O and filtered to give the title compound as a beige solid (8.43 g, 14.0 mmol). The mother liquor was concentrated in vacuo and purified by flash chromatography (gradient: EtOAc/hex 0-40%) to give the title compound as a light orange solid (4.07 g, 6.74 mmol). The solids obtained through trituration and flash chromatography were combined to give the title compound as a light orange solid (12.50 g, 89%) $^1$H NMR (400 MHz, CDCl3) δ ppm 8.65 (d, J=2.8 Hz, 1H), 8.55 (dd, J=4.6, 1.4 Hz, 1H), 7.98 (s, 1H), 7.78-7.73 (m, 1H), 7.46-7.40 (m, 1H), 6.50 (s, 1H), 3.89 (d, J=6.8 Hz, 2H), 2.30-2.15 (m, 3H), 2.02-1.93 (m, 2H), 1.50 (s, 3H), 1.45 (s, 9H), 1.38 (s, 9H); MS ESI [M+H]+ 604.3, calcd for [C27H34BrN5O6+H]+ 604.2.

(1s,3s)-3-(((3-bromo-5-(pyridin-3-yloxy)pyrazolo[1,5-a]pyrimidin-7-yl)(4-methoxybenzyl)amino)methyl)-1-methylcyclobutanol

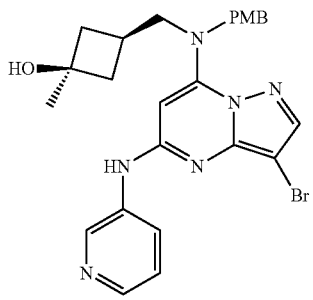

To a solution of (1s,3s)-3-(((3-bromo-5-chloropyrazolo[1,5-a]pyrimidin-7-yl)(4-methoxybenzyl)amino)methyl)-1-methylcyclobutanol (13.1 g, 28.2 mmol) and 3-hydroxypyridine (4.0 g, 42.3 mmol) in DMF (70 mL) was added K2CO3 (7.8 g, 56.3 mmol). The resulting mixture was stirred at 80° C. for 22 h. A mixture of 60% NaH (0.6 g, 15 mmol) and 3-hydroxypyridine (1.4 g, 14.7 mmol) in DMF was stirred at rt for 30 min before adding to the reaction mixture. The resulting solution was stirred at 100° C. for 20 h. Water and EtOAc were added to separate the phases and the aqueous phase was extracted with EtOAc. The combined organic extracts were washed with water, dried over MgSO4, filtered and concentrated. The crude product was purified by flash chromatography (gradient: EtOAc/hexanes 10-100%) using three columns in parallel. Impure fractions were collected and purified by flash chromatography (gradient: EtOAc/hexanes 50-100%). Pure fractions were combined and concentrated to give the desired product as a pale yellow solid (9.5 g, 64%). $^1$H NMR (400 MHz, CDCl3) δ ppm 8.56 (d, J=4 Hz, 1H), 8.45 (d, J=8 Hz, 1H), 8.00 (s, 1H), 7.69-7.65 (m, 1H), 7.36 (dd, J=4.8, 0.4 Hz, 1H), 7.19 (d, J=8.7 Hz, 2H), 6.85 (d, J=8.7 Hz, 2H), 5.71 (s, 1H), 4.91 (s, 2H), 3.87 (d, J=6.7 Hz, 2H), 3.87 (s, 3H), 2.30-2.15 (m, 3H), 1.77 (t, J=8.1 Hz, 2H), 1.37 (s, 3H); MS ESI [M+H]+ 524.2, calcd for [C25H26BrN5O3+H]+ 524.1.

N-cyclopropyl-4-(7-((((1s,3s)-3-hydroxy-3-methylcyclobutyl)methyl)(4-methoxybenzyl)amino)-5-(pyridin-3-yloxy)pyrazolo[1,5-a]pyrimidin-3-yl)-2-methylbenzamide

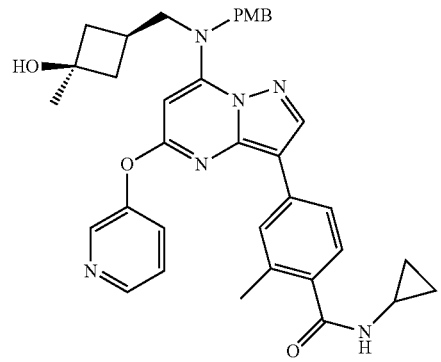

A mixture of (1s,3s)-3-(((3-bromo-5-(pyridin-3-yloxy)pyrazolo[1,5-a]pyrimidin-7-yl)(4-methoxybenzyl)amino)methyl)-1-methylcyclobutanol (9.5 g, 18.1 mmol), N-cyclopropyl-2-methyl-4-(4,4,5,5-tetramethyl-1,3,2-dioxaborolan-2-yl)benzamide (7.6 g, 25.4 mmol), 2M K3PO4 (23 mL, 45.3 mmol) in THF (100 mL) was purged with Ar for 10 min before the addition of PdCl2dppf·DCM (1.5 g, 1.8 mmol). The resulting mixture was heated under reflux in an oil bath at 84° C. for 16 h. The reaction mixture was diluted with DCM and sat. NaHCO3. The aqueous phase was extracted with DCM and the combined organic extracts were dried over MgSO4, filtered and concentrated. The crude product was purified by flash chromatography (gradient: EtOAc/hex 50-100%) using three columns in parallel. Impure fractions were collected and purified by flash chromatography using the above conditions. Pure fractions were combined and concentrated to give the desired product as an orange solid (9.6 g, 85%). 1H NMR (400 MHz, CDCl3) δ ppm 8.90-8.84 (m, 1H), 8.55 (d, J=4.5 Hz, 1H), 8.29 (s, 1H). 7.88-7.83 (m, 1H), 7.63 (s, 1H), 7.58-7.53 (m, 2H), 7.35-7.31 (m, 1H), 7.23 (d, J=8.6 Hz, 2H), 6.89 (d, J=8.6 Hz, 2H), 6.19 (br. s, 1H), 5.82 (s, 1H), 4.99 (s, 2H), 3.90 (d, J=10.0 Hz, 2H), 3.80 (s, 3H), 2.93-2.90 (m, 1H), 2.40 (s, 3H), 2.36-2.28 (m, 1H), 2.22-2.20 (m, 2H), 1.89-1.88 (m, 1H), 1.80 (t, J=8.7 Hz, 2H), 1.38 (s, 3H), 0.88-0.85 (m, 2H), 0.68-0.64 (m, 2H); MS ESI 619.3 [M+H]⁺, calcd for [C₃₆H₃₈N₆O₄+H]+ 619.3.

Preparation of Exemplary Compounds of the Invention

A1: N-cyclopropyl-4-(7-((cyclopropylmethyl)amino)-5-(((1S,2R)-2-hydroxycyclohexyl)amino)pyrazolo[1,5-a]pyrimidin-3-yl)-2-methylbenzamide hydrochloride

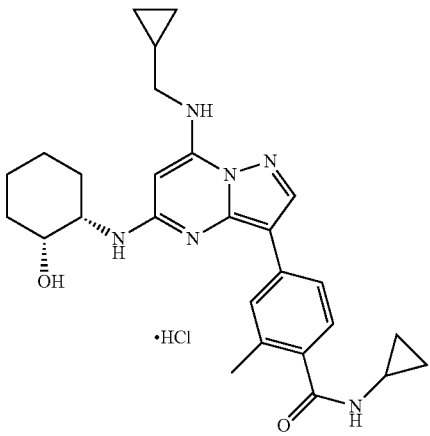 [SMILES: Cc1cc(-c2cnn3c(NCC4CC4)cc(N[C@H]4CCCC[C@H]4O)nc23)ccc1C(=O)NC1CC1 ; Cl]

A mixture of tert-butyl (3-bromo-5-(((1S,2R)-2-hydroxy-cyclohexyl)amino)pyrazolo[1,5-a]pyrimidin-7-yl)(cyclopropylmethyl)carbamate (8.48 g, 17.7 mmol), N-cyclopropyl-2-methyl-4-(4,4,5,5-tetramethyl-1,3,2-dioxaborolan-2-yl)benzamide (6.92 g, 23.0 mmol), PdCl₂dppf·DCM (1.44 g, 1.76 mmol), and 2M K₃PO₄ (26.6 mL, 106.2 mmol) in THF (60 mL) was divided and sealed into four microwave vials. Each vial was charged with Ar and heated in the microwave at 125° C. for 3 h. Water and EtOAc were added to separate the phases and the aqueous phase was extracted with EtOAc. The combined organic extracts were dried over Na₂SO₄, filtered and concentrated. The crude product was purified by flash chromatography (gradient: EtOAc/hex 20-100%) using two columns in parallel to give a yellow solid.

The above compound was dissolved in DCM (20 mL) and treated with TFA (20 mL) at rt for 1 h. After reaction completion, solvent was removed in vacuo and the crude was redissolved in DCM (20 mL), neutralized with saturated aqueous sodium bicarbonate and extracted with EtOAc. The combined organic extracts were dried over NaSO₄, filtered and concentrated. The crude product was purified by flash chromatography (gradient: 50-100% EtO Ac/hex then MeOH/DCM 0-10%) and triturated with Et₂O to give the title compound as a free base (white solid). The free base was dissolved in a mixture of DCM (25 mL) and MeOH (50 mL), HCl (1M Et₂O, 2 equiv) was then added slowly. Solvent was removed in vacuo to give the title compound as a pale yellow solid in HCl salt (2.09 g, 25% over 2 steps). ¹H NMR (400 MHz, CD₃OD) δ ppm 8.21 (s, 1H), 7.51-7.37 (m, 3H), 5.67 (br. s, 1H), 4.04-3.82 (m, 2H), 3.46-3.37 (m, 2H), 2.93-2.82 (m, 1H), 2.47 (s, 3H), 1.89-1.64 (m, 6H), 1.61-1.42 (m, 2H), 1.31-1.21 (m, 1H), 0.88-0.78 (m, 2H), 0.70-0.58 (m, 4H), 0.46-0.36 (m, 2H); MS ESI [M+H]⁺ 475.3, calcd for [C₂₇H₃₄N₆O₂+H]⁺ 475.3. HPLC purity: 98% at 254 nm.

A2: N-cyclopropyl-4-(7-((cyclopropylmethyl)amino)-5-(pyridin-3-yloxy)pyrazolo[1,5-a]pyrimidin-3-yl)-2-methylbenzamide hydrochloride

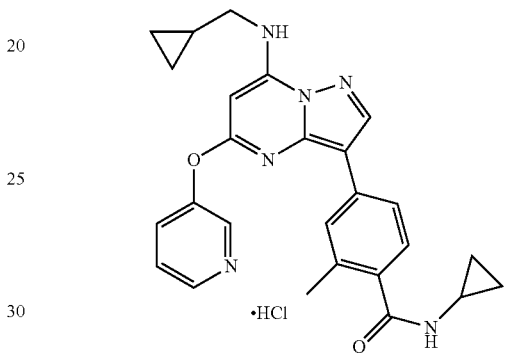

A mixture of tert-butyl (3-bromo-5-(pyridin-3-yloxy)pyrazolo[1,5-a]pyrimidin-7-yl)(cyclopropylmethyl)carbamate (367 mg, 0.80 mmol)), N-cyclopropyl-2-methyl-4-(4,4,5,5-tetramethyl-1,3,2-dioxaborolan-2-yl)benzamide (289 mg, 0.96 mmol), PdChdppf·DCM (65 mg, 0.080 mmol), and 2M K₃PO₄ (1.4 mL, 2.8 mmol) in THF (4 mL) was sealed into a microwave vial. The vial was charged with Ar and heated in the microwave at 130° C. for 4 h. Water and EtOAc were added to separate the phases and the aqueous phase was extracted with EtOAc. The combined organic extracts were dried over Na₂SO₄, filtered and concentrated. The crude product was purified by flash chromatography (gradient: EtOAc/hex 20-100%) to give a yellow oil.

The above compound was dissolved in DCM (6 mL) and treated with TFA (2 mL) at rt for 1 h. After reaction completion, solvent was removed in vacuo and the crude was redissolved in MeOH (4 mL), filtered, and purified by prep HPLC. The fractions were passed through a PoraPak column and triturated with Et₂O to give the title compound as a free base (white solid, 119 mg). A portion of the free base (67 mg, 0.15 mmol) was then dissolved in MeOH (10 mL), and HCl (1M Et₂O, 2 equiv) was then added slowly. The mixture was concentrated and triturated with Et₂O to give the title compound as a yellow solid in HCl salt (55 mg, 25% yield over 2 steps). ¹H NMR (400 MHz, CD₃OD) δ ppm 9.10 (s, 1H), 8.82 (d, J=6.0 Hz, 1H), 8.73-8.66 (m, 1H), 8.41 (s, 1H), 8.24-8.15 (m, 1H), 7.69 (s, 1H), 7.60 (d, J=8.3 Hz, 1H), 7.23 (d, J=8.0 Hz, 1H), 6.07 (s, 1H), 3.39 (d, J=7.0 Hz, 2H), 2.89-2.78 (m, 1H), 2.29 (s, 3H), 1.37-1.23 (m, 1H), 0.86-0.75 (m, 2H), 0.70-0.56 (m, 4H), 0.45-0.38 (m, 2H); MS ESI [M+H]⁺ 455.2, calcd for [C₂₆H₂₆N₆O₂+H]⁺ 455.2. HPLC purity: 95.9% at 254 nm.

A3: 4-(5-(cyclopentylamino)-7-((((1s,3s)-3-hydroxy-3-methylcyclobutyl)methyl)amino)pyrazolo[1,5-a]pyrimidin-3-yl)-N-cyclopropyl-2-methylbenzamide hydrochloride

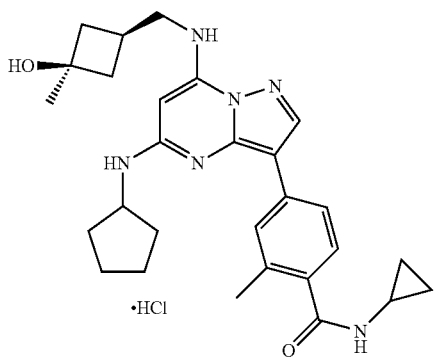 [SMILES: Cc1cc(-c2cnn3c(NC[C@H]4C[C@@](C)(O)C4)cc(NC4CCCC4)nc23)ccc1C(=O)NC1CC1 ; Cl]

A mixture of tert-butyl (3-bromo-5-(cyclopentylamino)pyrazolo[1,5-a]pyrimidin-7-yl)(((1s,3s)-3-((tert-butoxycarbonyl)oxy)-3-methylcyclobutyl)methyl)carbamate (0.40 g, 0.67 mmol), N-cyclopropyl-2-methyl-4-(4,4,5,5-tetramethyl-1,3,2-dioxaborolan-2-yl)benzamide (0.26 g, 0.88 mmol), PdCl$_2$dppf·DCM (0.055 g, 0.067 mmol), and 2M K$_3$PO$_4$ (1 mL, 2.01 mmol) in THF (4 mL) was charged with Ar and heated in the microwave at 130° C. for 3 h. Water and EtOAc were added to separate the phases and the aqueous phase was extracted with EtOAc. The combined organic extracts were dried over Na$_2$SO$_4$, filtered and concentrated. The crude product was purified by flash chromatography (gradient: EtOAc/hex 20-100%) to give a yellow oil.

The above compound was dissolved in DCM (10 mL) and treated with TFA (3 mL) at rt for 3 h. After reaction completion, solvent was removed in vacuo and the crude product was dissolved in MeOH (5 mL). The mixture was filtered and purified by prep-HPLC. The compound was passed through a PoraPak cartridge and triturated with Et$_2$O to give the title compound as a free base (white solid). The free base was dissolved in MeOH (5 mL), and HCl (1M Et$_2$O, 2 equiv) was then added slowly. Solvent was removed in vacuo to give the title compound as a light orange solid in HCl salt (75 mg, 21% over 2 steps). $^1$H NMR (400 MHz, CD$_3$OD) δ ppm 8.18 (s, 1H), 7.42 (s, 3H), 5.52 (br. s, 1H), 4.23-4.11 (m, 1H), 3.68-3.54 (m, 2H), 2.93-2.81 (m, 1H), 2.46 (s, 3H), 2.38-2.27 (m, 1H), 2.26-2.07 (m, 4H), 1.99-1.89 (m, 2H), 1.88-1.59 (m, 6H), 1.35 (s, 3H), 0.86-0.79 (m, 2H), 0.66-0.58 (m, 2H); MS ESI [M+H]$^+$ 489.4, calcd for [C$_{28}$H$_{36}$N$_6$O$_2$+H]$^+$ 489.3. HPLC purity: 99% at 254 nm.

A4: N-cyclopropyl-4-(7-((((1s,3s)-3-hydroxy-3-methylcyclobutyl)methyl)amino)-5-(pyridin-3-yloxy)pyrazolo[1,5-a]pyrimidin-3-yl)-2-methylbenzamide hydrochloride and its free base

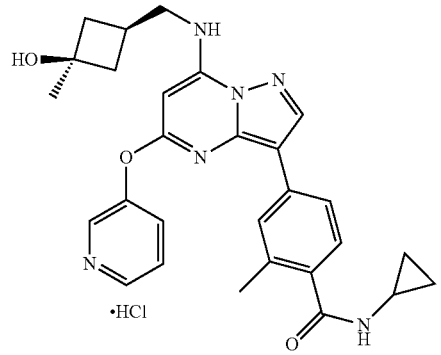 [SMILES: Cc1cc(-c2cnn3c(NC[C@H]4C[C@@](C)(O)C4)cc(Oc4cccnc4)nc23)ccc1C(=O)NC1CC1 ; Cl]

A). Through Boc deprotection: A mixture of tert-butyl (3-bromo-5-(pyridin-3-yloxy)pyrazolo[1,5-a]pyrimidin-7-yl)(((1s,3s)-3-((tert-butoxycarbonyl)oxy)-3-methylcyclobutyl)methyl)carbamate (0.23 g, 0.38 mmol), N-cyclopropyl-2-methyl-4-(4,4,5,5-tetramethyl-1,3,2-dioxaborolan-2-yl)benzamide (0.15 g, 0.49 mmol), PdC$_2$dppf·DCM (0.15 g, 0.49 mmol), and 2M K$_3$PO$_4$ (0.57 mL, 1.14 mmol) in THF (4 mL) was charged with Ar and heated in the microwave at 130° C. for 3 h. Water and EtOAc were added to separate the phases and the aqueous phase was extracted with EtOAc. The combined organic extracts were dried over NaSO$_4$, filtered and concentrated. The crude product was purified by flash chromatography (gradient: EtOAc/hex 20-60%) to give a yellow oil.

The above intermediate was dissolved in DCM (10 mL) and treated with TFA (3 mL) at rt for 3 h. After reaction completion, solvent was removed in vacuo and the crude product was dissolved in MeOH (5 mL). The mixture was filtered and purified by prep-HPLC. The compound was passed through a PoraPak cartridge and triturated with Et$_2$O to give the title compound as a free base (white solid). The free base was dissolved in MeOH (5 mL), and HCl (1 M Et$_2$O, 2 equiv) was then added slowly. Solvent was removed in vacuo to give the title compound as a beige solid in HCl salt (96 mg, 47% over 2 steps). $^1$H NMR (400 MHz, CD$_3$OD) δ ppm 9.14 (br. s, 1H), 8.89-8.82 (m, 1H), 8.79-8.71 (m, 1H), 8.40 (s, 1H), 8.31-8.21 (m, 1H), 7.68 (s, 1H), 7.59 (d, J=9.5 Hz, 1H), 7.23 (d, J=8.0 Hz, 1H), 6.06 (s, 1H), 3.56 (d, J=6.5 Hz, 2H), 2.88-2.79 (m, 1H), 2.40-2.31 (m, 1H), 2.29 (s, 3H), 2.26-2.18 (m, 2H), 1.99-1.89 (m, 2H), 1.37 (s, 3H), 0.85-0.76 (m, 2H), 0.63-0.53 (m, 2H); MS ESI [M+H]$^+$ 499.3, calcd for [C$_{28}$H$_{30}$N$_6$O$_3$+H]$^+$ 499.2. HPLC purity: 99.5% at 254 nm.

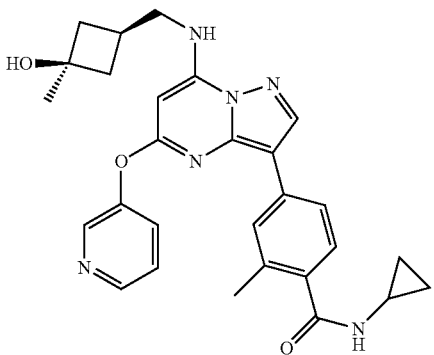 [SMILES: Cc1cc(-c2cnn3c(NC[C@H]4C[C@@](C)(O)C4)cc(Oc4cccnc4)nc23)ccc1C(=O)NC1CC1]

B). Through PMB deprotection: A mixture of N-cyclopropyl-4-(7-((((1s,3s)-3-hydroxy-3-methylcyclobutyl)methyl)(4-methoxybenzyl)amino)-5-(pyridin-3-yloxy)pyrazolo[1,5-a]pyrimidin-3-yl)-2-methylbenzamide (9.6 g, 15.5 mmol), TFA (50 mL) in DCE (70 mL) was heated in an oil bath at 50° C. for 4 h. After reaction completion, solvent was removed in vacuo and the crude product was dissolved in a mixture of MeOH/DCM (100 mL/25 mL). 2M Na$_2$CO$_3$ (150 mL) was then added and the resulting mixture was stirred at rt for 30 min. The reaction mixture was diluted with DCM and the phases were separated. The aqueous phase was extracted with DCM and the combined organic extracts were washed with water, dried over MgSO$_4$, filtered and concentrated. The crude product was triturated and sonicated in a mixture of DCM/Et$_2$O (10 mL/70 mL) to give the title compound as a off white solid in free base (5.9 g, 77%). $^1$H NMR (400 MHz, CD$_3$OD) δ ppm 8.58-8.53 (m, 1H), 8.50-8.46 (m, 1H), 8.36 (s, 1H), 7.86-7.80 (m, 1H), 7.76-7.72 (m, 1H), 7.61-7.55 (m, 2H), 7.18 (d, J=8.0 Hz, 1H), 5.92 (s, 1H), 3.52 (d, J=6.8 Hz, 2H), 2.86-2.77 (m, 1H), 2.38-2.28 (m, 1H), 2.25 (s, 3H), 2.24-2.18 (m, 2H), 1.99-1.88 (m, 2H), 1.37 (s, 3H), 0.84-0.75 (m, 2H), 0.64-0.54 (m, 2H); MS ESI [M+H]$^+$ 499.2, calcd for [C$_{28}$H$_{30}$N$_6$O$_3$+H]$^+$ 499.2. HPLC purity: 96.1% at 235 nm.

The following final compounds were synthesized similarly to the syntheses of A1-4.

| Structure | Example number<br>MS calcd;<br>MS ESI [M + H]$^+$<br>Salt Form;<br>HPLC purity | $^1$H NMR |
|---|---|---|
| 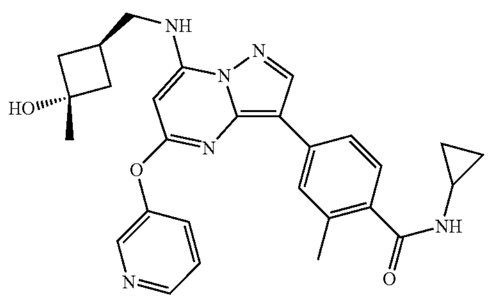 [SMILES: Cc1cc(-c2cnn3c(NC[C@H]4C[C@](C)(O)C4)cc(Oc4cccnc4)nc23)ccc1C(=O)NC1CC1] | A5<br>[C$_{28}$H$_{30}$N$_6$O$_3$ + H]$^+$<br>499.2;<br>499.3;<br>free base;<br>98.9% at 254 nM | (400 MHz, CD$_3$OD) δ ppm 8.55 (dd, J = 2.8, 0.4 Hz, 1H), 8.47 (dd, J = 4.8, 1.6 Hz, 1H), 8.33 (s, 1 H), 7.83-7.80 (m, 1H), 7.72 (s, 1H), 7.58-7.55 (m, 2H), 7.18 (d, J = 8.0 Hz, 1H), 5.89 (s, 1H), 3.49 (d, J = 7.6 Hz, 2H), 2.87-2.78 (m, 2H), 2.28-2.23 (m, 5H), 1.97-1.92 (m, 2H), 1.36 (s, 3H), 0.82-0.77 (m, 2H), 0.62-0.58 (m, 2H). |
| 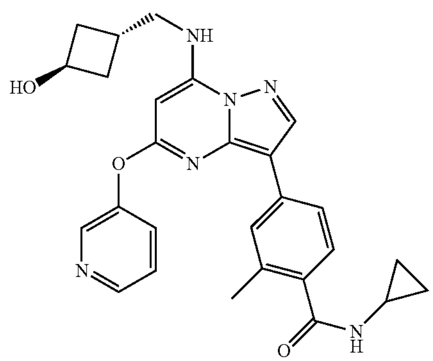 [SMILES: Cc1cc(-c2cnn3c(NC[C@H]4C[C@H](O)C4)cc(Oc4cccnc4)nc23)ccc1C(=O)NC1CC1] | A6<br>[C$_{27}$H$_{28}$N$_6$O$_3$ + H]$^+$<br>485.2;<br>485.3;<br>HCl salt;<br>98.8% at 254 nm | (400 MHz, CD$_3$OD) δ ppm 9.13 (d, J = 2.3 Hz, 1H), 8.86 (d, J = 5.8 Hz, 1H), 8.77-8.69 (m, 1H), 8.40 (s, 1H), 8.26 (dd, J = 8.8, 5.8 Hz, 1H), 7.67 (s, 1H), 7.59 (d, J = 8.0 Hz, 1H), 7.24 (d, J = 8.0 Hz, 1H), 6.07 (s, 1H), 4.53-4.39 (m, 1H), 3.57 (d, J = 8.0 Hz, 2H), 2.89-2.79 (m, 1H), 2.76-2.61 (m, 1H), 2.30 (s, 3H), 2.29-2.21 (m, 2H), 2.21-2.08 (m, 2H), 0.85-0.78 (m, 2H), 0.65-0.58 (m, 2H). |

| Structure | Example number<br>MS calcd;<br>MS ESI [M + H]+<br>Salt Form;<br>HPLC purity | $^1$H NMR |
|---|---|---|
| (structure) | A8<br>[$C_{27}H_{34}N_6O_2$ + H]+<br>475.3;<br>475.4;<br>HCl salt;<br>99.3% at 254 nm | (400 MHz, CD$_3$OD) δ ppm 8.22 (s, 1H), 7.51-7.36 (m, 3H), 5.68 (s, 1H), 3.77 (s, 2H), 3.37-3.33 (m, 2H), 2.93-2.84 (m, 1H), 2.47 (s, 3H), 2.07-1.95 (m, 4H), 1.93-1.72 (m, 4H), 1.34-1.19 (m, 1H), 0.88-0.78 (m, 2H), 0.69-0.59 (m, 4H), 0.45-0.37 (m, 2H). |
| (structure) | A11<br>[$C_{27}H_{28}N_6O_3$ + H]+<br>485.2<br>485.2;<br>HCl salt;<br>98.6% at 254 nm | (400 MHz, CD$_3$OD) δ ppm 9.14 (s, 1H), 8.85 (d, J = 5.5 Hz, 1H), 8.79-8.72 (m, 1H), 8.40 (s, 1H), 8.30-8.21 (m, 1H), 7.68 (s, 1H), 7.59 (d, J = 7.8 Hz, 1H), 7.23 (d, J = 8.0 Hz, 1H), 6.06 (s, 1H), 4.17-4.06 (m, 1H), 3.54 (d, J = 6.5 Hz, 2H), 2.88-2.78 (m, 1H), 2.53-2.43 (m, 2H), 2.29 (s, 4H), 1.81-1.68 (m, 2H), 0.84-0.77 (m, 2H), 0.62-0.56 (m, 2H). |
| (structure) | A12<br>[$C_{27}H_{34}N_6O_2$ + H]+<br>475.3;<br>475.4;<br>HCl salt;<br>97.5% at 254 nm | (400 MHz, CD$_3$OD) δ ppm 8.18 (s, 1H), 7.55-7.29 (m, 3H), 5.54 (br, s, 1H), 4.50-4.37 (m, 1H), 4.26-4.07 (m, 1H), 3.62 (d, J = 6.8 Hz, 2H), 2.92-2.83 (m, 1H), 2.75-2.61 (m, 1H), 2.46 (s, 3H), 2.31-2.02 (m, 6H), 1.92-1.56 (m, 6H), 0.91-0.75 (m, 2H), 0.71-0.52 (m, 2H). |
| (structure) | A13<br>[$C_{28}H_{36}N_6O_2$ + H]+<br>489.3;<br>489.4<br>TFA salt;<br>98.2% at 254 nm | (400 MHz, CD$_3$OD) δ ppm 8.18 (s, 1H), 7.48-7.36 (m, 3H), 5.52 (s, 1H), 4.23-4.10 (m, 1H), 3.65-3.57 (m, 2H), 2.93-2.75 (m, 2H), 2.46 (s, 3H), 2.31-2.21 (m, 2H), 2.20-2.11 (m, 3H), 2.06-1.89 (m, 2H), 1.89-1.50 (m, 6H), 1.37 (s, .3H), 0.87-0.79 (m, 2H), 0.68-0.56 (m, 2H). |

Example B

TTK Inhibition Assay

Active TTK was purchased from Invitrogen as an amino terminal GST fusion of full length human TTK. Amino terminal 6 histidine, sumo tagged human TTK (residues 1-275) was expressed in *E. coli*, and purified to >95% homogeneity by $Ni^{2+}$ agarose, gel filtration, and ion exchange chromatography.

TTK activity was measured using an indirect ELISA detection system. GST-TTK (0.68 nM) was incubated in the presence of either 16 μM ATP (Sigma cat #A7699) or 100 μM ATP, 50 mM Hepes pH 7.2, 1 mM EGTA, 10 mM $MgCl_2$, and 0.1% Pluronic in a 96 well microtitre plate pre-coated with amino terminal 6 histidine, sumo tagged TTK (amino acid residues 1-275).

The reaction was allowed to proceed for 30 minutes, followed by 5 washes of the plate with Wash Buffer (phosphate buffered saline supplemented with 0.2% Tween 20), and incubation for 30 minutes with a 1:3000 dilution of primary antibody (Cell Signaling cat #9381). The plate was washed 5 times with Wash Buffer, incubated for 30 minutes in the presence of secondary antibody coupled to horse radish peroxidase (BioRad cat #1721019, 1:3000 concentration), washed an additional 5 times with Wash Buffer, and incubated in the presence of TMB substrate (Sigma cat #T0440). The colourimetric reaction was allowed to continue for 5 minutes, followed by addition of stop solution (0.5 N sulphuric acid), and quantified by detection at 450 nm with either a monochromatic or filter based plate reader (Molecular Devices M5 or Beckman DTX880, respectively).

Compound inhibition was determined at either a fixed concentration (10 μM) or at a variable inhibitor concentration (typically 0.5 μM to 0.001 μM in a 10 point dose response titration). Compounds were pre-incubated in the presence of enzyme for 5 minutes prior to addition of ATP and the activity remaining quantified using the above described activity assay. The % Inhibition of a compound was determined using the following formula; % Inhibition=100×(1−(experimental value−background value)/(high activity control−background value)). The $IC_{50}$ value was determined using a non-linear 4 point logistic curve fit (XLfit4, IDBS) with the formula; $(A+(B/(1+((x/C)^D))))$, where A=background value, B=range, C=inflection point, D=curve fit parameter.

In Table 1 below, $IC_{50}$ value ranges for exemplary compounds are given using 100 uM ATP. The $IC_{50}$ ranges are indicated as "A," "B," and "C," for values less than or equal to 0.1 μM; those greater than 0.1 μM and less than or equal to 0.5 μM; and those greater than 0.5 μM, respectively. $IC_{50}$ ranges denoted with an asterisk indicated that 16 μM ATP (Sigma cat #A7699) was used in the assay.

Example C

Cancer Cell Line Data on Exemplary Compounds of the Invention

Breast cancer cells (MDA-MB-468), colon cancer cells (HCT116) and ovarian cancer cells (OVCAR-3) were seeded (1000 to 4000 in 80 μl per well depending on the cell growth rate) into 96 well plates 24 hours before compound overlay. Compounds were prepared as 10 mM stock solutions in 100% DMSO which were diluted with DMEM (Dulbecco's Modified Eagle's Medium) cell growth Medium (Invitrogen, Burlington, ON, Canada) containing 10% FBS (Fetal Bovine Serum) to concentrations ranging from 50 nM to 250 μM. Aliquots (20 μl) from each concentration were overlaid to 80 μl of the pre-seeded cells in the 96 well plates to make final concentrations of 10 nM to 50 μM. The cells were cultured for 5 days before the Sulforhodamine B assay (SRB) was performed to determine the compound's cell growth inhibition activity.

Sulforhodamine B (purchased from Sigma, Oakville, ON, Canada) is a water-soluble dye that binds to the basic amino acids of the cellular proteins. Thus, colorimetric measurement of the bound dye provides an estimate of the total protein mass that is related to the cell number, the cells are fixed in situ by gently aspirating off the culture media and adding 50 μl ice cold 10% Trichloroacetic Acid (TCA) per well and incubate at 4° C. for 30-60 min, The plates are washed with $H_2O$ five times and allowed to air dry for 5 min. Addition of 50 μl 0.4% (w/v) SRB solution in 1% (v/v) acetic acid to each well and incubatation for 30 min at RT completes the staining reaction. Following staining, plates are washed four times with 1% acetic acid to remove unbound dye and then allowed to air dry for 5 min. The stain is solubilized with 100 μl of 10 mM Tris pH 10.5 per well. Absorbance is read at 570 nm.

The percentage (%) of relative growth inhibition was calculated by comparing to DMSO treated only cells (100%). $GI_{50}$'s were determined for compounds with cytotoxic activity. The $GI_{50}$ was calculated using GraphPad PRISM software (GraphPad Software, Inc., San Diego, Calif., USA). $GI_{50}$ (growth inhibition) is the compound concentration that causes 50% inhibition of cell growth.

In Table 1 below, $GI_{50}$ value ranges for compound examples against breast cancer cell lines (MDA-MB-468), colon cancer cell lines (HCT116) and ovarian cancer cell lines (OVCAR-3) are given. The example compounds demonstrated varying growth inhibition/cell killing activity against cells of breast cancer, colon cancer, and ovarian cancer. The $GI_{50}$ ranges are indicated as "A," "B," and "C," for values less than or equal to 0.1 μM; those greater than 0.1 μM and less than or equal to 0.5 μM; and those greater than 0.5 μM, respectively.

Example D

Colon and Ovarian Cancer Tumor-Initiating Cell Data of Exemplary Compounds

Materials and Methods: Non-tissue or tissue cultured treated T-75 flask and 96-well plates were purchased from VWR. Vitamin B-27 supplement, MEM NEAA (minimum essential medium non-essential amino acids), sodium pyruvate, L-glutamine, N2 supplement, penicillin-streptomycin and fungizone/amphotericin B were obtained from Invitrogen. Lipid mixture, heparin and EGF were purchased from Sigma; bFGF from BD Biosciences. Tumor Initiating Cells (TICs) from colon were routinely maintained using non-tissue cultured treated T-75 flasks in DMEM:F12 medium containing 0.2×B-27 supplement, 4 ug/ml heparin, 1×MEM NEAA, 1× sodium pyruvate, 1 mM glutamine, 10 pg/ul bFGF, 20 pg/ul EGF, 1× N2 supplement, lipid mixture, penicillin-streptomycin and fungizone/amphotericin B. Ovarian TICs were routinely maintained using tissue cultured treated T-75 flasks in DMEM:F12 medium containing 1×B-27 supplement, 4 ug/ml heparin, 20 pg/ul bFGF, 20 pg/ul EGF and penicillin-streptomycin.

Assay Protocol: Compounds described herein were dissolved in DMSO and further diluted in cell culture medium for GI$_{50}$ determination. Colon TICs were trypsinized and seeded into non-tissue cultured treated 96-well plates with 4,000 cells/well. After 24 h, compound was added into the cell culture at different concentrations, and the final concentration of DMSO was adjusted to 0.1%. Cells were then cultured at 37° C. for 9 days. Ovarian TICs were trypsinized and seeded into tissue cultured treated 96-well plates with 1,000 cells/well. After 24 h, compound was added into the cell culture at different concentrations, and the final concentration of DMSO was adjusted to 0.1%. Cells were then cultured at 37° C. for 6 days. Cell viability was assessed by Alamar Blue assay: 10 ul of Alamar Blue was added into each well. After 4 hours incubation at 37° C., fluorescence was recorded at excitation 544 and emission 590. GI$_{50}$ (Growth inhibition) was calculated using GraphPad Prism 4.0 software. Cell growth inhibition data for compounds described herein is tabulated below.

In Table 1 below, GI$_{50}$ value ranges for compound examples against TICs (Colon 12 and Ovarian 2393A) are given. The GI$_{50}$ ranges are indicated as "A," "B," and "C," for values less than or equal to 0.1 µM; those greater than 0.1 µM and less than or equal to 0.5 µM; and those greater than 0.5 µM, respectively.

TABLE 1

In vitro activity of Compound Examples

| Example # | TTK IC$_{50}$ Range | Cancer Cell Line GI$_{50}$ Range | | | Tumor Initiating Cell GI$_{50}$ Range | |
|---|---|---|---|---|---|---|
| | | MDA-MB-468 | HCT116 | OVCAR-3 | Ovarian 2393A | Colon 12 |
| A1 | A | A | A | A | A | A |
| A2 | A | A | A | A | ND | ND |
| A3 | A | A | A | A | ND | ND |
| A4 | A | A | A | A | A | ND |
| A5 | A | A | A | B | ND | ND |
| A6 | A | A | A | A | A | A |
| A8 | A | B | B | C | ND | ND |
| A11 | A | A | A | A | ND | ND |
| A12 | A | A | A | A | ND | ND |
| A13 | A | B | A | B | ND | ND |

ND—not determined

What is claimed is:

1. A method for treating cancer, the method comprising administering to a subject in need thereof an effective amount of a compound represented by the following structural formula:

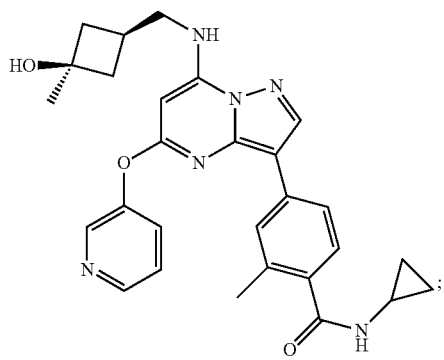 [SMILES: Cc1cc(-c2cnn3c(NC[C@H]4C[C@@](C)(O)C4)cc(Oc4cccnc4)nc23)ccc1C(=O)NC1CC1]

or a pharmaceutically acceptable salt thereof, wherein the cancer is pancreatic cancer, prostate cancer, lung cancer, melanoma, colon cancer, ovarian cancer, hepatocellular carcinoma, mesothelioma, leukemia, lymphoma or glioblastoma multiform.

2. The method of claim 1, wherein the cancer is pancreatic cancer.

3. The method of claim 1, wherein the cancer is prostate cancer.

4. The method of claim 1, wherein the cancer is lung cancer.

5. The method of claim 1, wherein the cancer is melanoma.

6. The method of claim 1, wherein the cancer is colon cancer.

7. The method of claim 1, wherein the cancer is ovarian cancer.

8. The method of claim 1, wherein the cancer is hepatocellular carcinoma.

9. The method of claim 1, wherein the cancer is mesothelioma.

10. The method of claim 1, wherein the cancer is leukemia.

11. The method of claim 1, wherein the cancer is lymphoma.

12. A method for treating cancer, the method comprising administering to a subject in need thereof an effective amount of a compound represented by the following structural formula:

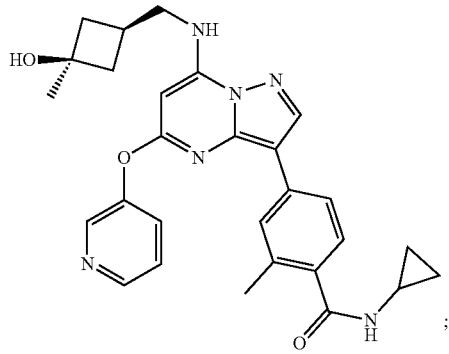 [SMILES: Cc1cc(-c2cnn3c(NC[C@H]4C[C@@](C)(O)C4)cc(Oc4cccnc4)nc23)ccc1C(=O)NC1CC1]

or a pharmaceutically acceptable salt thereof, wherein the cancer is breast cancer.

13. The method of claim 12, wherein the breast cancer is luminal B sub-type breast cancer.

14. The method of claim 12, wherein the breast cancer is basal sub-type breast cancer.

15. A method for treating cancer, the method comprising administering to a subject in need thereof an effective amount of a compound represented by the following structural formula:

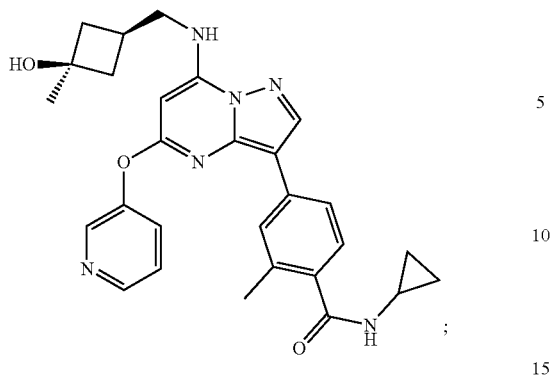
or a pharmaceutically acceptable salt thereof, wherein the cancer is ER (estrogen receptor), HER2 and PR (progesterone receptor) negative breast cancer.
16. The method of claim 1, wherein the cancer is glioblastoma multiform.
* * * * *